United States Patent
Long et al.

(10) Patent No.: US 11,406,363 B2
(45) Date of Patent: Aug. 9, 2022

(54) BIOPSY DEVICE

(71) Applicant: National University of Ireland, Galway, Galway (IE)

(72) Inventors: Damien Long, Galway (IE); Edmund Brennan, Nenagh (IE); Jimmy Eaton-Evans, Na Forbacha (IE); Jonathan Bouchier-Hayes, Dublin (IE)

(73) Assignee: NATIONAL UNIVERSITY OF IRELAND, Galway (IE)

( * ) Notice: Subject to any disclaimer, the term of this patent is extended or adjusted under 35 U.S.C. 154(b) by 67 days.

(21) Appl. No.: 16/472,496

(22) PCT Filed: Dec. 21, 2017

(86) PCT No.: PCT/EP2017/084243
§ 371 (c)(1),
(2) Date: Jun. 21, 2019

(87) PCT Pub. No.: WO2018/115368
PCT Pub. Date: Jun. 28, 2018

(65) Prior Publication Data
US 2020/0187919 A1 Jun. 18, 2020

(30) Foreign Application Priority Data
Dec. 21, 2016 (EP) ..................... 16205976

(51) Int. Cl.
*A61B 10/02* (2006.01)
*A61B 10/04* (2006.01)

(52) U.S. Cl.
CPC ...... *A61B 10/0233* (2013.01); *A61B 10/0275* (2013.01); *A61B 10/04* (2013.01); *A61B 2010/0208* (2013.01); *A61B 2010/045* (2013.01)

(58) Field of Classification Search
None
See application file for complete search history.

(56) References Cited

U.S. PATENT DOCUMENTS

| 4,177,797 A | 12/1979 | Baylis et al. |
| 4,306,570 A | 12/1981 | Matthews |

(Continued)

FOREIGN PATENT DOCUMENTS

| CA | 2 926 63 8 A1 | 9/2004 |
| CN | 2030089 U | 1/1989 |

(Continued)

OTHER PUBLICATIONS

International Search Report and Written Opinion dated Apr. 19, 2018 in counterpart PCT International Application No. PCT/EP2017/084243.

(Continued)

*Primary Examiner* — Benjamin S Melhus
(74) *Attorney, Agent, or Firm* — Brian J. Colandreo; Jeffrey T. Placker; Holland & Knight LLP

(57) ABSTRACT

A biopsy device (100), comprising: a cannula (102) comprising an elongate cannula body (106) extending between a cannula distal end (108) and a cannula proximal end (110) to define a lumen (112), wherein the cannula comprises a cutting portion at the cannula distal end (108); a stylet (104) comprising an elongate body (116) having a stylet distal end (118) and a stylet proximal end (120), the stylet (104) being slidably disposed within the lumen (112), wherein the stylet (104) comprises a tissue sampling portion (122); and an alignment means (126) arranged to maintain a preferred alignment between the stylet (104) and the cannula (102), wherein the alignment means (126) is arranged to align one or more of: i) relative rotation between the stylet distal end and the cannula distal end; ii) relative flexing between the stylet distal end and the cannula distal end; and iii) relative (Continued)

axial translation between the stylet distal end and the cannula distal end.

15 Claims, 15 Drawing Sheets

(56) References Cited

U.S. PATENT DOCUMENTS

| | | | |
|---|---|---|---|
| 4,735,215 A | 4/1988 | Goto et al. | |
| 4,881,551 A | 11/1989 | Taylor | |
| 4,976,269 A | 12/1990 | Mehl | |
| 5,161,542 A | 11/1992 | Palestrant | |
| 5,271,414 A * | 12/1993 | Parti | A61B 10/0266 600/567 |
| 5,316,013 A * | 5/1994 | Striebel, II | A61B 10/0275 606/171 |
| 5,660,186 A | 8/1997 | Bachir | |
| 5,916,229 A | 6/1999 | Evans | |
| 5,961,534 A | 10/1999 | Banik et al. | |
| 5,976,164 A | 11/1999 | Bencini et al. | |
| 6,015,391 A * | 1/2000 | Rishton | A61B 10/0266 600/562 |
| 6,083,237 A | 7/2000 | Huitema et al. | |
| 6,419,641 B1 * | 7/2002 | Mark | A61B 10/0275 600/564 |
| 7,048,694 B2 * | 5/2006 | Mark | A61B 10/0275 600/564 |
| 7,704,234 B2 * | 4/2010 | Darr | A61M 25/0138 604/164.01 |
| 7,722,549 B2 * | 5/2010 | Nakao | A61B 17/32002 600/564 |
| 7,803,142 B2 * | 9/2010 | Longson | A61M 25/065 606/108 |
| 8,506,503 B2 | 8/2013 | Fritscher-Ravens et al. | |
| 8,568,334 B2 | 10/2013 | Field et al. | |
| 8,979,803 B2 * | 3/2015 | Darr | A61B 10/0275 604/164.1 |
| 9,788,819 B2 * | 10/2017 | Householder | A61B 10/0233 |
| 10,463,380 B2 * | 11/2019 | Purdy | A61B 17/1631 |
| 10,478,241 B2 * | 11/2019 | Purdy | A61B 17/1671 |
| 10,736,613 B2 * | 8/2020 | Dejima | A61B 10/04 |
| 2002/0151821 A1 | 10/2002 | Castellacci | |
| 2003/0093007 A1 | 5/2003 | Wood | |
| 2003/0125639 A1 * | 7/2003 | Fisher | A61B 10/0275 600/564 |
| 2003/0208136 A1 * | 11/2003 | Mark | A61B 10/0275 600/564 |
| 2004/0054377 A1 | 3/2004 | Foster et al. | |
| 2004/0133124 A1 * | 7/2004 | Bates | A61B 10/0275 600/564 |
| 2007/0016099 A1 * | 1/2007 | Chin | A61B 10/0275 600/565 |
| 2008/0281226 A1 * | 11/2008 | Peters | A61B 10/0275 600/567 |
| 2008/0319468 A1 | 12/2008 | Shabaz et al. | |
| 2009/0118641 A1 | 5/2009 | Van Dam et al. | |
| 2009/0326412 A1 * | 12/2009 | Pakter | A61B 10/0266 600/567 |
| 2010/0114031 A1 * | 5/2010 | Jarial | A61B 10/0275 604/164.11 |
| 2010/0130850 A1 | 5/2010 | Pakter | |
| 2010/0305470 A1 * | 12/2010 | Ireland | A61B 10/0275 600/567 |
| 2011/0046512 A1 | 2/2011 | Bacon et al. | |
| 2011/0098595 A1 | 4/2011 | Hibner | |
| 2011/0190660 A1 | 8/2011 | Levy | |
| 2012/0022568 A1 * | 1/2012 | Koblish | A61B 10/025 606/185 |
| 2012/0059247 A1 | 3/2012 | Speeg et al. | |
| 2012/0065543 A1 | 3/2012 | Ireland | |
| 2012/0197157 A1 | 8/2012 | Ryan et al. | |
| 2012/0226101 A1 | 9/2012 | Tinkham et al. | |
| 2012/0245487 A1 | 9/2012 | Eells et al. | |
| 2013/0006141 A1 | 1/2013 | Sigmon, Jr. | |
| 2013/0006144 A1 | 1/2013 | Clancy et al. | |
| 2013/0035609 A1 * | 2/2013 | Darr | A61M 25/0138 600/567 |
| 2013/0046201 A1 | 2/2013 | Stanley et al. | |
| 2013/0158429 A1 * | 6/2013 | Lee-Sepsick | A61B 10/04 600/570 |
| 2013/0225996 A1 * | 8/2013 | Dillard | A61B 10/0283 600/439 |
| 2014/0026693 A1 | 1/2014 | Eller | |
| 2014/0171825 A1 | 6/2014 | Eller et al. | |
| 2014/0257136 A1 | 9/2014 | Leahy et al. | |
| 2014/0371626 A1 | 12/2014 | Hibner et al. | |
| 2015/0018844 A1 | 1/2015 | Harris | |
| 2015/0032129 A1 | 1/2015 | Oostman, Jr. et al. | |
| 2015/0080759 A1 | 3/2015 | DiCarlo | |
| 2015/0133815 A1 | 5/2015 | McGhie | |
| 2015/0141868 A1 | 5/2015 | Clark et al. | |
| 2015/0272556 A1 * | 10/2015 | Lee | A61B 10/04 600/566 |
| 2015/0297198 A1 | 10/2015 | Bierhoff et al. | |
| 2015/0313579 A1 | 11/2015 | Householder et al. | |
| 2015/0335319 A1 | 11/2015 | Chin et al. | |
| 2016/0030019 A1 * | 2/2016 | Faulkner | A61B 10/0275 600/567 |
| 2016/0089208 A1 * | 3/2016 | Vetter | A61B 17/3207 606/130 |

FOREIGN PATENT DOCUMENTS

| | | |
|---|---|---|
| CN | 2142325 Y | 9/1993 |
| CN | 2243268 Y | 12/1996 |
| CN | 2289521 Y | 9/1998 |
| CN | 2368459 Y | 3/2000 |
| CN | 2449658 Y | 9/2001 |
| CN | 2822524 Y | 10/2006 |
| CN | 202568323 U | 12/2012 |
| CN | 104486985 A | 4/2015 |
| EP | 2 848 220 A1 | 3/2015 |
| EP | 3 020 340 A1 | 5/2016 |
| MX | 2011009680 A | 2/2012 |
| WO | WO 2004/006789 A1 | 1/2004 |
| WO | WO 2004/062505 A1 | 7/2004 |
| WO | WO 2007/029013 A2 | 3/2007 |
| WO | WO 2011/097374 A1 | 8/2011 |
| WO | WO 2013/003087 A1 | 1/2013 |
| WO | WO 2014/020150 A1 | 2/2014 |
| WO | WO 2014/058667 A1 | 4/2014 |
| WO | WO 2014/136045 A1 | 9/2014 |
| WO | WO 2015/156450 A1 | 10/2015 |
| WO | WO 2015/183663 A1 | 12/2015 |
| WO | WO 2016/085423 A1 | 6/2016 |

OTHER PUBLICATIONS

European Search Report dated Jun. 20, 2017 in counterpart European Application No. 16205976.0.

* cited by examiner

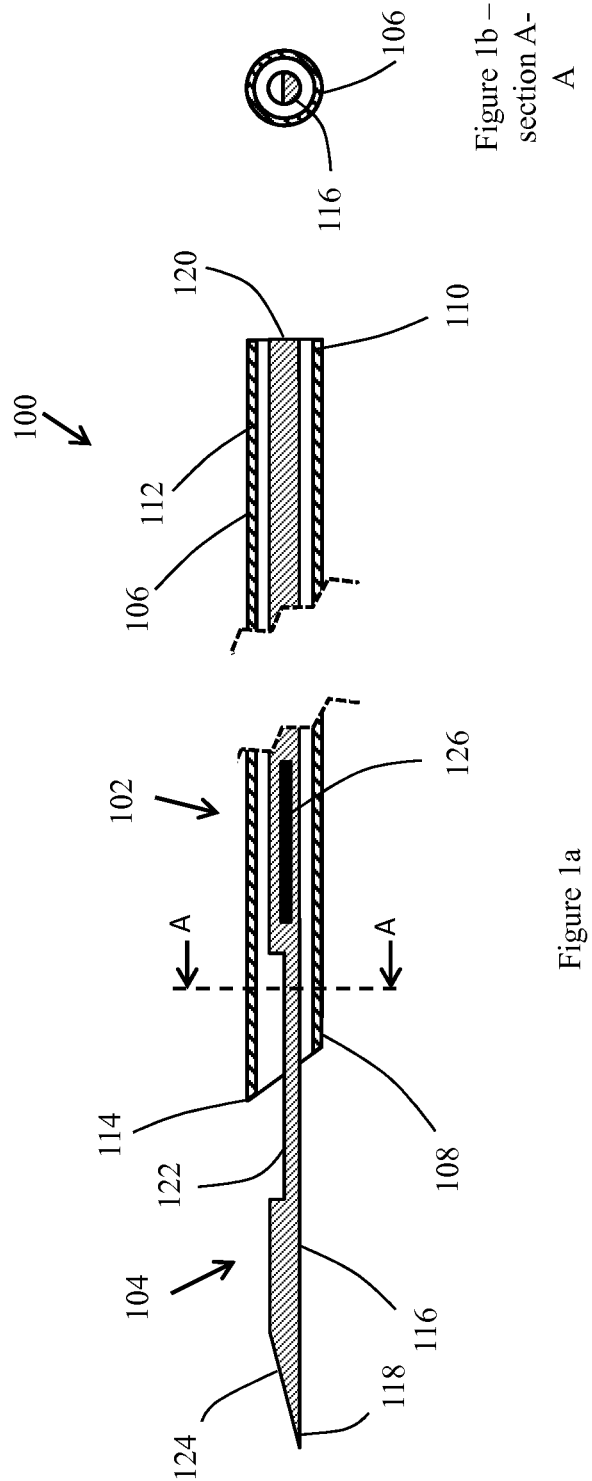

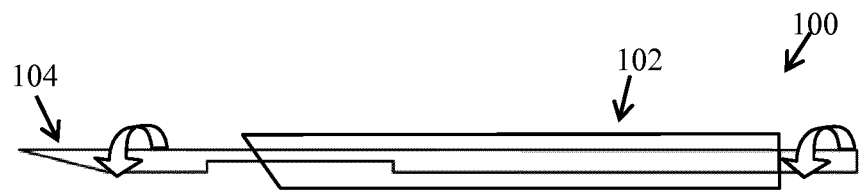
Figure 2a
Figure 2b(i)
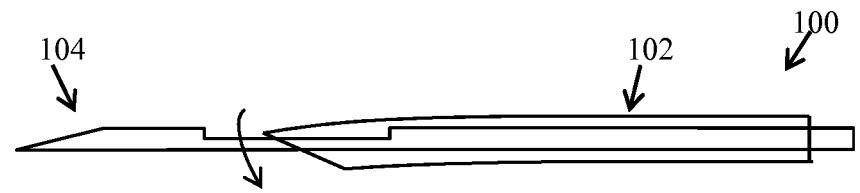
Figure 2b(ii)
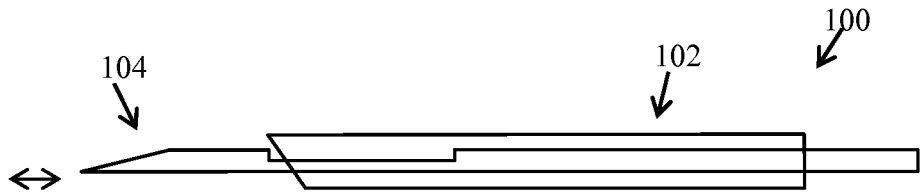
Figure 2c
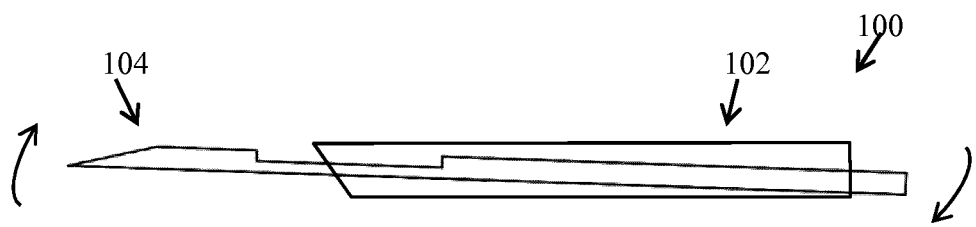
Figure 2d
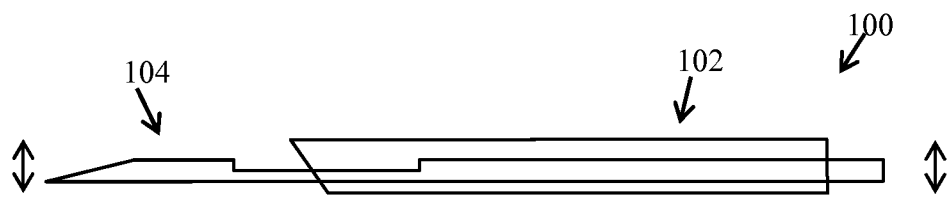
Figure 2e

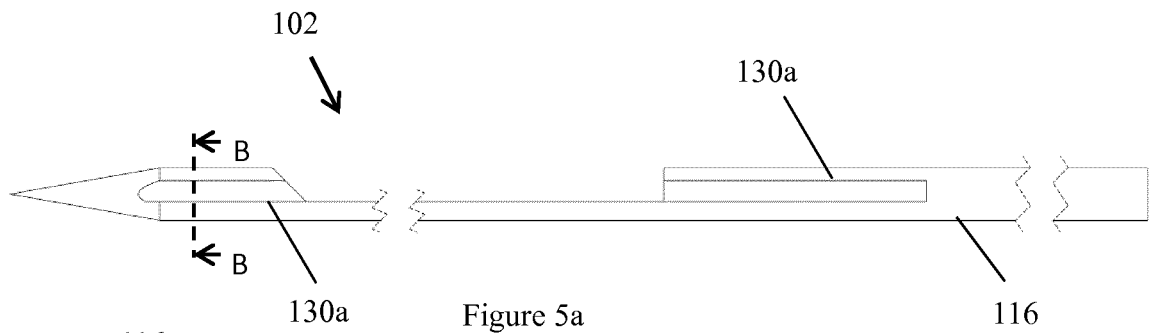
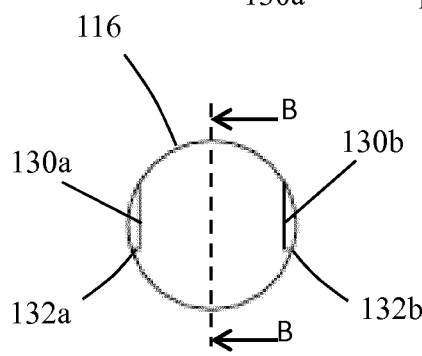
Figure 5b – enlarged section B-B
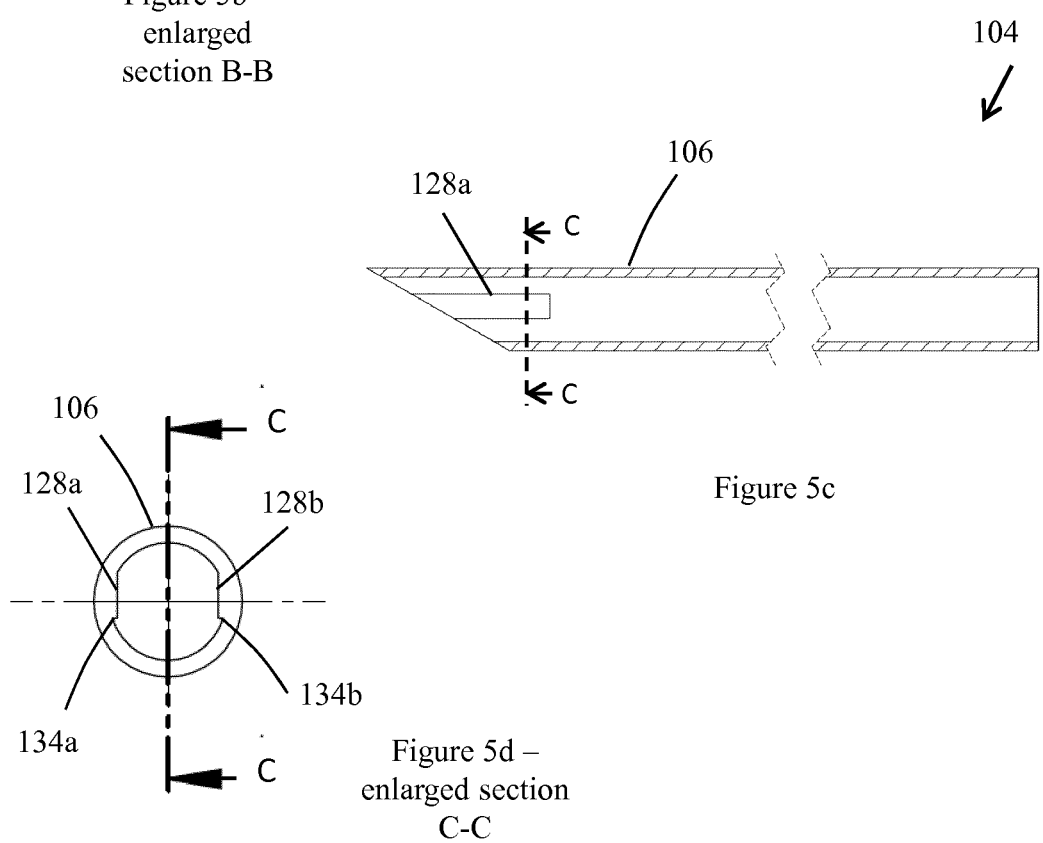
Figure 5c
Figure 5d – enlarged section C-C

BIOPSY DEVICE

The present application relates to a biopsy device. The biopsy device may be a flexible biopsy device that is suitable for use with an endoscope.

The present application relates to the field of biopsy devices that may be used to take a tissue sample from the body, for example percutaneously, transluminally or endoscopically. Such tissue sampling can include cytological or histological analysis depending on the amount of tissue structure preserved by the biopsy device.

Known biopsy devices include those used for endoscopic ultrasound fine-needle aspiration (EUS-FNA). EUS-FNA devices typically comprise a long, thin metallic needle housed within a tubular sheath. The distal end of the needle can be moved in and out of the sheath by means of a sliding mechanism in a handle of the device.

During an EUS-FNA procedure, an endoscope may be positioned in the GI tract adjacent to the area of interest (typically a lesion in or around the pancreas). With the needle point fully withdrawn into the sheath, the EUS-FNA device is threaded through the endoscope until it exits the distal end of the scope. The needle is then advanced out of the sheath and, using an ultra-sound probe built into the distal end of the endoscope, is guided through the wall of the GI tract and into the area of interest. The needle of such an EUS-FNA device can typically advance up to 8 cm beyond the tip of the protective sheath.

Loose cells are then suctioned or aspirated through the cannula of the FNA needle. This material is then expressed onto a slide for subsequent diagnostic analysis by a cytologist. With such a cytology analysis, tissue architecture is not present and therefore cytology samples aspirated through a needle provide significantly less diagnostic information than if the clinician were able to acquire a solid core of tissue for histological analysis.

A number of prior art endoscopic devices have been specifically developed with the intent of acquiring histological samples. These may be known in the art as Fine Needle Biopsy (FNB) needles.

One prior art example of an EUS-FNB needle as described in US2003236471 (A1) operates on a side-cutting principle analogous to that of a cheese grater. As such, it typically does not obtain a true tissue core with preserved architecture, but rather a continuous strip of macerated tissue shavings and congealed blood cells.

Biopsy devices are also known that allow percutaneous acquisition of a high quality tissue core sample suitable for histological analysis using a two part biopsy needle. The biopsy needle has an inner part or stylet having a tissue collecting or specimen notch formed near a stylet distal end. An outer part or cannula has a point on a cannula distal end and encloses the stylet. The cannula and stylet are arranged so that the cannula point advances over the stylet in order to cover the specimen notch. In use, advancement of the stylet through tissue will first result in tissue prolapsing into the recessed notch. Subsequent forward movement of the cannula cuts out a specimen of the prolapsed tissue, so that the specimen becomes retained in the specimen notch of the stylet. The biopsy needle may then be withdrawn and the tissue sample recovered from the stylet. These devices may incorporate a spring-loaded handle to advance the cannula over the stylet very quickly in order to prevent the prolapsed tissue in the specimen notch from being displaced as the cannula advances over the stylet.

Typically these prior art devices are inherently rigid due to their construction from a steel tube (outer cannula) and a mandrel (inner stylet) and as such they are more suited to biopsies that can be taken in a relatively straight configuration. However, the majority of pancreatic lesions occur in the head and uncinate process and often require a duodenal approach. The lack of flexibility of the prior art percutaneous biopsy needles therefore precludes them from practical access to these sites. In general, this technology is best suited to percutaneous applications, and is sub-optimal for transluminal applications where significant anatomical bends are typically present.

The addition of flexible elements (e.g. a spiral cut outer cannula) can help to overcome the limitations in flexibility associated with endoscopic use of these two part percutaneous biopsy needles. However, such a biopsy device may experience misalignment of the inner and outer parts at the point where a sample is to be taken (cannula distal end and stylet distal end) because of the long length and different flexural properties of the two components. Such a device is therefore not optimised for endoscopic use and the efficiency of the cutting can be significantly affected by its long length and flexing of the needle components.

In a first aspect, the present application provides a biopsy device, comprising: a cannula comprising an elongate cannula body extending between a cannula distal end and a cannula proximal end to define a lumen, wherein the cannula comprises a cutting portion at the cannula distal end; a stylet comprising an elongate body having a stylet distal end and a stylet proximal end, the stylet being slidably disposed within the lumen, wherein the stylet comprises a tissue sampling portion; and an alignment means arranged to maintain a preferred alignment between the stylet and cannula distal ends, wherein the alignment means is arranged to align one or both of: i) relative rotation between the stylet distal end and the cannula distal end; and ii) relative flexing between the stylet distal end and the cannula distal end, wherein the alignment means comprises a coupling mechanism arranged to couple the stylet and the cannula, the coupling mechanism comprising at least one raised portion of the stylet or the cannula, and at least one corresponding recessed portion of the other of the stylet or the cannula, the coupling mechanism being at least partly provided at or near the cannula distal end and the stylet distal end and wherein engagement between the at least one raised portion and the at least one recessed portion is arranged to resist movement of the cannula and stylet away from the preferred alignment.

By providing an alignment means formed by a mechanical coupling mechanism acting between the cannula and stylet the alignment between them can be improved. The mechanical coupling mechanism provides alignment in addition to that which would be provided by a close-matching fit between the stylet and the cannula lumen or any coupling which is provided between them at their proximal ends. As discussed below, the mechanical coupling may help to reduce a number of different modes of misalignment. By helping to ensure the cannula and stylet distal ends remain in the preferred alignment the tissue sample can be more effectively collected.

In a second aspect, the present application provides a biopsy device, comprising: a cannula comprising an elongate cannula body extending between a cannula distal end and a cannula proximal end to define a lumen, wherein the cannula comprises a cutting portion at the cannula distal end; a stylet comprising an elongate body having a stylet distal end and a stylet proximal end, the stylet being slidably disposed within the lumen, wherein the stylet comprises a tissue sampling portion; and an alignment means arranged to maintain a preferred alignment between the stylet and cannula distal ends, wherein the alignment means is arranged to resist relative rotation between the stylet distal end and the cannula distal end, wherein the alignment means comprises a coupling mechanism arranged to couple the stylet and the cannula, the coupling mechanism comprising a portion of the body of the stylet and a portion of the lumen of the cannula each having a corresponding non-circular cross section, wherein engagement between the cannula body and the stylet body resists relative rotation between them.

The portion of the body of the stylet and the portion of the lumen of the cannula having a corresponding non-circular cross section may each at least partly be provided at or near the cannula distal end and the stylet distal end.

In a third aspect, the present application discloses: a biopsy device, comprising: a cannula comprising an elongate cannula body extending between a cannula distal end and a cannula proximal end to define a lumen, wherein the cannula comprises a cutting portion at the cannula distal end; a stylet comprising an elongate body having a stylet distal end and a stylet proximal end, the stylet being slidably disposed within the lumen, wherein the stylet comprises a tissue sampling portion; and an alignment means arranged to maintain preferred alignment between the stylet and the cannula, wherein the alignment means is arranged to align one or more of: i) relative rotation between the stylet distal end and the cannula distal end; ii) relative flexing between the stylet distal end and the cannula distal end; and iii) relative axial translation between the stylet distal end and the cannula distal end.

The biopsy device of the present application provides an alignment means to help ensure correct alignment between a cannula having a cutting portion and a stylet having a tissue sampling portion. The alignment means may aid effective cutting and receiving of tissue in the sample receiving portion by reducing misalignment between the cannula and stylet. This may help provide a sample which retains significant tissue structure suitable for histological analysis.

Misalignment between the cannula and stylet may occur, for example, by relative rotation, flexing, tilting or translation between the stylet and cannula. This may in particular be a problem for flexible biopsy devices used for endoscopy, but may also occur in more rigid devices suited to percutaneous use. Relative rotation can be caused by the stylet having a preferred plane in which it tends to flex (e.g. because of the properties of its shape and construction) which is different to that of the cannula (which typically has no preferred planar direction of flexing or may have a different preferred planar direction of flexing). This may result in sub-optimal orientation of the cutting cannula relative to the stylet.

As well as rotation, misalignment of the stylet and cannula can also occur due to relative flexing, titling or translation (either axial translation along the length of the biopsy device, or radial translation perpendicular to the length of the biopsy device) of each component during use. For example, when the stylet is extended from the distal end of the cannula to allow tissue collection the stylet may be pushed away from alignment with the cannula (e.g. the stylet may flex, tilt or translate such that it is no longer concentrically aligned with the cannula). This can happen when the stylet encounters resistance in the tissue being sampled that causes its path to deviate. The alignment means may help ensure correct alignment between the cutting portion of the cannula and the tissue receiving portion of the stylet, thereby aiding effective cutting and sample collection. The alignment means may, for example, reduce the risk of the stylet colliding with an inner wall of the cannula body, or the cutting portion gouging tissue collected in the tissue receiving portion (e.g. the cutting portion may otherwise plough or lift the sample if not in the preferred alignment), during relative movement to collect the sample.

The features of any of the following statements can be combined with each other and used with the biopsy devices of any of the first, second or third aspects defined above.

Optionally, the alignment means is arranged to maintain preferred alignment between the cutting portion of the cannula and the stylet, and preferably between the cutting portion of the cannula and the tissue sampling portion of the stylet.

Optionally, the cutting portion comprises a tissue piercing portion, and the alignment means is arranged to maintain preferred alignment between the tissue piercing portion and the stylet and preferably between the tissue piercing portion and the tissue sampling portion of the stylet.

Optionally, the alignment means is arranged to align at least one or both of a relative position or orientation of the stylet and the cannula.

Optionally, the cannula has a preferred cutting orientation in relation to the orientation of the stylet, and wherein the alignment means is arranged to align the cannula and stylet in the preferred cutting orientation relative to each other. Optionally, the cannula has a preferred cutting orientation and the stylet has a preferred tissue sampling orientation, and wherein the alignment means is arranged to align the preferred cutting orientation with the preferred sampling orientation. This may aid effective cutting of the tissue by aligning a tissue piercing portion of the cannula cutting portion with the tissue sampling portion of the stylet.

Optionally, the stylet has a preferred plane of flexibility, and wherein the alignment means is arranged to resist relative movement between the stylet and the cannula in the preferred plane of flexibility. This may reduce or prevent the stylet flexing in its preferred plane of flexibility towards or away from the cannula when a tissue sample is being taken. In other embodiments, this may, for example, allow the cannula and stylet to flex to the same degree so that the alignment between them is maintained.

Optionally, the alignment means comprises a coupling mechanism arranged to couple the stylet and the cannula. This may provide a mechanical engagement to link the stylet and the cannula.

Optionally, the coupling mechanism comprises at least one raised portion of the body of the stylet or the body of the cannula, and at least one corresponding recessed portion of the other of the body of the stylet or the body of the cannula.

Optionally, the recessed portion comprises a groove extending part way through the body of the cannula or body of the stylet. This may allow both rotational and flexural alignment of the cannula and stylet. For example, it may help to resist flexing of the stylet away from alignment with the cannula, and at the same time resist relative rotation between them.

Optionally, the recessed portion may comprise a groove extending part way through the body of the cannula or body of the stylet and optionally the recessed portion may comprise a slot extending through the body of the cannula or body of the stylet.

Optionally, the raised portion may comprise at least one pin arranged to be received in the recessed portion.

Optionally, the raised portion may comprise at least one ridge on the body of the cannula or stylet arranged to be received in the recessed portion.

Optionally, the recessed portion may define a first abutment surface and the raised portion may define a second abutment surface, wherein contact between the first and second abutment surfaces resists relative flexing movement between the stylet and the cannula. The first and second abutment surfaces may be arranged to resist relative movement in a preferred plane of flexibility of the stylet. Engagement between the abutment surfaces may aid flexural alignment by forcing the stylet and the cannula to flex to the same degree, or by reducing flexing of the stylet away from alignment with the cannula during collection of a sample.

Optionally, the recessed portion defines a first distal stop surface and/or a first proximal stop surface, and the raised portion defines a second distal stop surface and/or a second proximal stop surface, wherein contact between the first and second proximal or distal stop surfaces restricts the range of axial movement between the stylet and the cannula along a longitudinal axis of the biopsy device.

Optionally, the cannula may comprise a distal region extending from the cannula distal end and the stylet may comprise a distal region extending from the stylet distal end, and wherein the coupling mechanism may be provided in the distal region of the cannula and the distal region of the stylet. The distal region of the cannula may extend from the cannula distal end a distance of up to or approximately equal to 25% of the distance between the cannula distal end and the cannula proximal end; and/or the distal region of the stylet may extend from the stylet distal end a distance of up to or approximately equal to 25% of the distance between the stylet distal end and the stylet proximal end. Preferably, the distal region of the cannula may extend from the cannula distal end a distance of up to or approximately equal to 50 mm; and/or the distal region of the stylet may extend from the stylet distal end a distance of up to or approximately equal to 50 mm.

Optionally, the stylet distal region may comprise a region of the stylet extending between the stylet distal end and a distal end of the tissue sampling portion.

Optionally, the raised portion or the recessed portion or both extend along the stylet or the cannula. This may allow the control of relative flexing, rotation, tilting, and radial translation, while still allowing relative sliding of the stylet within the lumen.

Optionally, the raised portion or the recessed portion or both extend from at or near the distal end of the stylet and/or the cannula. This may aid alignment of the distal ends of the cannula and stylet.

Optionally, the cannula proximal end and the stylet proximal end are rotationally uncoupled. This may help to reduce friction at the distal coupling of the stylet and cannula and allow them to more easily slide relative to each other in order to collect a tissue sample.

Optionally, the biopsy device may further comprise a control means arranged to control relative sliding between the cannula and stylet to allow a tissue sample to be taken. The control means may be arranged to link the cannula proximal end and the stylet proximal end to control relative axial sliding between them and to allow relative rotation between the cannula proximal end and the stylet proximal end. This may allow user manipulation of the stylet and cannula to collect a tissue sample, while allowing freedom for the cannula and stylet proximal ends to rotate freely relative to each other. This may help to reduce tension build up in the coupling mechanism acting to align them at their distal ends, which may help to reduce friction between the cannula and stylet.

Optionally, the control means may comprise an actuator arranged to slide the cannula relative to the stylet to collect a tissue sample. This may allow convenient collecting of a tissue sample. The alignment means may be advantageous in combination with a biased actuator. The alignment means may act to limit any misalignment that may result from the force and rapid movement of the cannula and/or stylet by the biased actuator.

Optionally, the coupling mechanism comprises a portion of the body of the stylet and a portion of the lumen of the cannula each having a corresponding non-circular cross section, wherein engagement between the cannula body and the stylet body resists relative rotation between them.

Optionally, the alignment means comprises a biasing mechanism arranged to bias the flexing of the cannula in a plane corresponding to a preferred plane of flexibility of the stylet. This may encourage the cannula to flex in the same direction as the stylet to aid alignment.

Optionally, the biasing mechanism comprises at least one flexibility control portion of the cannula body.

Optionally, the flexibility control portion comprises a weakened portion of the cannula body formed by one or more slots in the body of the cannula.

Optionally, the one or more slots are disposed on the cannula body such that flexibility of the cannula is increased in a plane corresponding to a preferred plane of flexibility of the stylet. This may bias the flexing of the cannula such that it matches that of the stylet.

Optionally, the one or more slots comprise a first set of slots and a second set of slots, the first and second set of slots being disposed on opposing sides of the cannula body. This may provide improved flexing of the cannula in the preferred plane of flexibility to match that of the stylet.

Optionally, the flexibility control portion overlaps the sampling portion when the distal end of the cannula and stylet are approximately longitudinally aligned. This may provide control of the flexing of the cannula at the position of the tissue sampling portion.

Optionally, the flexibility control portion is provided only on the cannula and not the stylet.

This may provide control of the flexing of the cannula, while not affecting the strength of the stylet.

Optionally, the cutting portion comprises a tissue piercing portion, and wherein the alignment means is arranged to prevent or minimise flexing of the cannula in a first direction towards the stylet to prevent or minimise movement of the tissue piercing portion towards the tissue sampling portion. This may prevent or reduce gouging of the tissue collected in the tissue sampling portion by the tissue piercing portion when it moves over the stylet.

Optionally, the alignment means comprises a first and second set of slots on opposing sides of the cannula body, and wherein at least one of the first and second sets of slots comprises at least one stop member arranged to resist flexing of the cannula relative to the stylet in the first direction and allow flexing of the cannula relative to the stylet in a second direction opposite to the first direction.

Optionally, the alignment means is further arranged to align one or both of: i) relative tilting between the stylet and the cannula; and ii) relative radial translation between the stylet and the cannula.

Optionally, the biopsy device may be suitable for endoscopic or transluminal use. Optionally, the cannula and stylet may be flexible, and further optionally the cannula may comprise a flexible portion to aid flexibility.

Embodiments of the invention will now be described, by way of example only, with reference to the accompanying drawings, in which:

FIG. 1a shows a schematic cross section view of a biopsy device according to an embodiment;

FIG. 1b shows a second schematic cross section view of the biopsy device shown in FIG. 1a;

FIGS. 2a to 2e show example modes of alignment between a cannula and a stylet of the biopsy device shown in FIG. 1a;

FIGS. 3a to 3c show examples of rotational alignment between a cannula and a stylet of the biopsy device shown in FIG. 1a;

FIGS. 4a to 4c show examples of flexural alignment between a cannula and a stylet of the biopsy device shown in FIG. 1a;

FIGS. 5a to 5g show an embodiment of a coupling mechanism used to align a cannula and a stylet of a biopsy device;

FIGS. 12a to 12e show the collection of a tissue sample using the biopsy device of FIG. 1a.

Figure 3A:
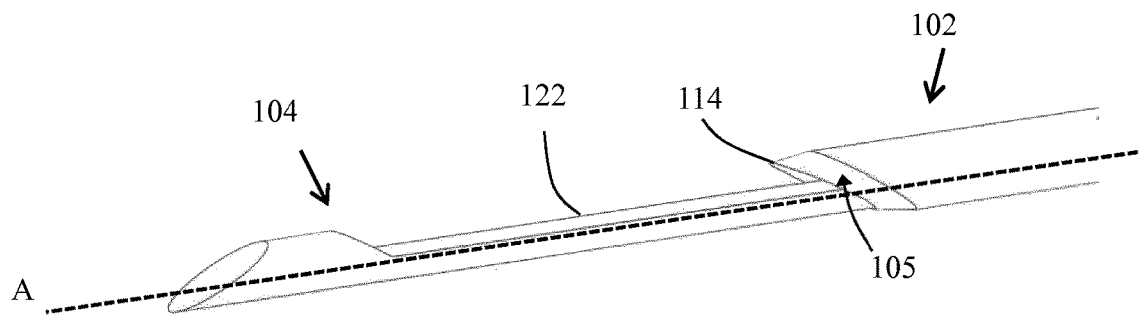

The present application relates to a biopsy device 100 for taking a tissue sample from the human or animal body. The biopsy device may be used with any suitable method of delivering a biopsy device to a site of interest where a tissue sample is to be taken. For example, the biopsy device may be suitable for endoscopic, transluminal or percutaneous use, or may be used with other methods of delivery as would be apparent to a person skilled in the field of the invention.

An embodiment of the biopsy device 100 is shown schematically in FIGS. 1a and 1b (not all of the length of the biopsy device is shown in FIGS. 1a and 1b as indicated by the broken lines). The biopsy device 100 generally comprises a cannula 102 and a stylet 104. The cannula 102 comprises an elongate cannula body 106, which extends between a cannula distal end 108 (the end nearest to the patient or biopsy site in use) and a cannula proximal end 110 (the end away from the patient). The cannula body 106 defines a lumen or hollow tube 112 extending from the cannula distal end 108 to the cannula proximal end 110. The cannula 102 further comprises a cutting portion 105 located at (or near) the cannula distal end 108. The cutting portion 105 may comprise one or more cutting edges adapted to cut tissue during use of the biopsy device 100 to obtain a sample.

In the described embodiment, the cutting portion 105 comprises a cutting edge extending around the circumference of the distal end of the cannula. In other embodiments, the cutting portion 105 may comprise a cutting edge extending around only part of the circumference of the cannula 102. The cutting portion 105 may comprise a tissue piercing portion 114 adapted to pierce tissue at the biopsy site. The tissue piercing portion 114 may comprise a point or protrusion of the cutting edge at a position around the circumference of the cannula distal end. In other embodiments, the tissue piercing portion may be formed by a needle tip or point. The tissue piercing portion is adapted to make first contact with the tissue during cutting to provide effective insertion into the tissue.

The stylet 104 comprises an elongate body 116 having a stylet distal end 118 and a stylet proximal end 120. The stylet 104 is slidably disposed within the lumen 112 such that it may slide along its length relative to the cannula 102. The stylet 104 further comprises a tissue sampling portion 122 adapted to receive a sample of tissue cut by the cannula cutting portion 105. The tissue sampling portion 122 may comprise a notch or slot in the body 116 of the stylet defining a cavity or recess in which tissue may be received. The tissue sampling portion 122 may be located near to the distal end 118 of the stylet 104 as shown in FIG. 1a. In other embodiments, the tissue sampling portion 122 may be spaced further apart from the distal end 118 of the stylet, or may be provided at the distal end 118. In the described embodiment, the stylet 104 further comprises a stylet cutting portion 124 to aid insertion of the stylet 104 into tissue during use of the biopsy device 100. In the described embodiment, the stylet cutting portion 124 is formed from a tapered portion of the stylet body 116 at the stylet distal end 118. In other embodiments, the stylet cutting portion 124 may be any other suitable shape to aid insertion of the stylet 104 into tissue during use. In yet other embodiments, the stylet cutting portion 124 may be absent.

In the described embodiment, the cannula 102 and stylet 104 are generally circular in cross section as shown in FIG. 1b. In such an embodiment, both the cannula body 106 and the stylet body 116 may have a generally circular cross section. In the described embodiment, the lumen 112 may also have a generally circular cross section to accommodate the stylet body 116. In other embodiments, the cannula body 106 may have any other suitable cross section, and may, for example, be elliptical or square. In other embodiments, the stylet body 116 and the lumen 112 may also have any other suitable cross section shape. In the described embodiment, the cross section of the stylet body 116 and the cannula body 106 is generally constant along their length. In yet other embodiments, the cross section may vary along the length of either the cannula body 106 and/or the stylet body 116 or the lumen 112. In the described embodiment, the lumen 112 is formed such that it is concentric with the cannula body 106 such that the cannula body 106 has a constant thickness. In yet other embodiments, the lumen 112 may be off-centre relative to a central axis of the cannula body i.e. the thickness of the cannula body 106 may vary around its circumference. In some embodiments, the cross section of the cannula 102 may be a different shape to that of the lumen 112.

In some embodiments, the cannula 102 and the stylet 104 may be made from metal such as stainless steel. In other embodiments, either the cannula 104, the stylet 102, or both may be made from any other suitable material such as cobalt-chromium alloys, Nitinol, or a combination thereof. In some embodiments, the combined stylet 104 and cannula 102 may be substantially rigid and inflexible. Such an embodiment may be suited to percutaneous or other straight-line use where significant bending of the biopsy device 100 is not required to reach the biopsy site. In other embodiments, the combined stylet 104 and cannula 102 may be substantially flexible. In such an embodiment, the biopsy device 100 is suited to pass through the working channel of an endoscope or the like. This may allow access to biopsy sites that are within the body and require bending of the biopsy device 100 to reach them. In some embodiments, the biopsy device 100 may further comprise an outer member surrounding the cannula body 106 along at least part of its length. The cannula may be arranged to slide relative to the outer member during use as will be described later. The outer member may, for example, form a protective sheath adapted to protect the inner wall of an endoscope working channel when the biopsy device 100 is passed along its length. In such an embodiment, the sheath may be made from a deformable material such as a polymer or the like to protect the endoscope or the user when handling the biopsy device.

One or both of the cannula body 106 and stylet body 116 may be formed at least partly from a flexible material. In some embodiments, in order to improve the flexibility of the biopsy device 100, the cannula 102 may comprise one or more flexible portions along at least part of the length of the cannula body 106. The flexible portions may comprise a weakened portion (or portions) of the cannula body 106 such as a spiral cut slotted section or a torque tube section. In some embodiments, the stylet 104 may also comprise similar flexible portion(s) to improve its flexibility. In other embodiments, the cannula 102 or stylet 104 may have a sufficient degree of flexibility due to their material of construction and physical size without the need for additional flexible portions.

At the proximal end 110 of the cannula 102 and proximal end 120 of the stylet 104 a control means (not shown in the Figures) may be provided to allow the biopsy device 100 to be manipulated during use. The control means may be arranged to facilitate manual or actuated control of the relative sliding between the cannula 102 and stylet 104 to allow a tissue sample to be taken. The control means may, for example, comprise a handle or grip adapted to allow the user to control and manipulate the position of the cannula 102 and stylet 104 during use. In some embodiments, the control means may comprise an actuator arranged to slide the cannula 102 relative to the stylet 104 to collect a tissue sample. Once the stylet 102 has been moved to an extended position from the end of the cannula 102, the actuator may be arranged to move the cannula 102 over the stylet 104 to collect a tissue sample. In some embodiments, the actuator may be biased by a spring or the like to provide a rapid cutting motion. In yet other embodiments, the actuator may be arranged to provide a first sliding movement in which the stylet 104 is moved relative to the cannula 102 such that it protrudes from the end of the cannula and enters the tissue at the biopsy site. The actuator may be arranged to then provide a second sliding movement of the cannula 102 relative to the stylet 104 to cut the tissue and collect a sample.

The biopsy device 100 further comprises an alignment means 126 arranged to maintain a preferred alignment between the stylet 104 and the cannula 102. The alignment means 126 is arranged to align the cannula distal end 108 and the stylet distal end 118. In the preferred alignment, the cannula 102 and the stylet 104 are aligned so that a tissue sample can be effectively taken using the biopsy device 100. The preferred alignment may, for example, constrain the cannula 102 and stylet 104 to move in a desired orientation and/or along a desired path relative to each other. The preferred alignment may, for example, enhance the ability of a tissue sample to be taken with preserved tissue architecture for histological analysis. In one example of a preferred alignment, the alignment between the tissue piercing portion 114 of the cannula 102 and the tissue sampling portion 122 of the stylet 104 may be maintained to ensure effective tissue sampling.

The alignment means 126 is arranged to act on the distal ends of the cannula 102 and stylet 104 and is provided in addition to any coupling between the cannula 102 and stylet 104 proximal ends. For example, in some embodiments, a coupling means may be provided to link the cannula and stylet proximal ends 110, 120 together and facilitate relative sliding motion between them. Although such a coupling between the stylet 104 and cannula 102 may align the cannula and stylet proximal ends 110, 120, it may not provide adequate alignment of the cannula and stylet distal ends 108, 118. This may, for example, be the case in embodiments where a long and/or flexible cannula 102 and stylet 104 are provided. The alignment means is also provided in addition to any alignment provided by a close fit between the stylet body and the inner surface of the lumen. The alignment means 126 is therefore provided in addition to any coupling linking the proximal ends of the cannula and stylet to provide alignment of the cannula and stylet distal ends to maintain the preferred alignment between them.

The cannula proximal end and the stylet proximal end may be rotationally uncoupled relative to each other. In some embodiments, one or both of the cannula and stylet may be proximally rotationally uncoupled from the control means or the actuator (i.e. any coupling between the cannula proximal end and the stylet proximal end is arranged to allow relative rotation between them, but may restrict or control other relative movement). For example, the cannula and the stylet may both be arranged to rotate freely relative to a handle forming the control means. In some embodiments, one of the cannula and stylet may be arranged to freely rotate, while the other may be rotationally fixed to the handle.

In such an embodiment, the control means may be arranged to allow relative rotation between the cannula proximal end and the stylet proximal end, but may control relative axial sliding to obtain a tissue sample. This may help to reduce a sideways or torsional stress being built up in the alignment means. By rotationally uncoupling the proximal ends of the cannula and/or stylet friction between them may be reduced so that the stylet can be easily translated within the cannula.

An example of a preferred alignment between the cannula 102 and stylet 104 is shown in FIGS. 1a and 1b. In this example, the tissue piercing portion 114 of the cannula 102 is aligned relative to the position of the tissue sampling portion 122 of the stylet 104 to aid collection of a tissue sample. In some embodiments, the alignment means 126 may be arranged to align at least one or both of a relative position or orientation of the stylet 104 and the cannula 102. The alignment means 126 may therefore prevent or reduce misalignment between the cannula 102 and stylet 104 during use to aid collection of a tissue sample. As shown in FIG. 1a, when the tissue sampling portion 122 is facing upwards (e.g. rotated to a 12 o'clock position so it is at the top of the biopsy device 100), the tissue piercing portion 114 is also rotated to a 12 o'clock position so that it is at the top of the biopsy device 100. This may allow the tissue piercing portion 114 to pierce the tissue in line with the tissue sampling portion to aid collection of the sample.

The alignment means 126 may be arranged to align one or more of a number of different modes of alignment between the cannula 102 and the stylet 104. The alignment means may be arranged to align any one or more of: i) rotation between the stylet 104 and the cannula 102 (shown in FIG. 2a); ii) flexing between the stylet 104 and the cannula 102 (shown in FIGS. 2b(i) and 2b(ii)); iii) axial translation between the stylet 104 and the cannula 102 in a direction along a longitudinal axis of the biopsy device (shown in FIG. 2c); iv) tilting between the stylet 104 and the cannula 102 (shown in FIG. 2d); and v) radial translation between the stylet 104 and the cannula 102 in a direction at least partly perpendicular to a longitudinal axis of the biopsy device (shown in FIG. 2e). These different modes of alignment are illustrated schematically in FIGS. 2a to 2e respectively, and described in more detail as follows. Each of the different modes of alignment may, for example, be caused by the stylet and/or cannula being manipulated in order to facilitate passage through tortuous anatomy and/or inhomogeneous tissue on the way to the biopsy site.

Figure 3B:
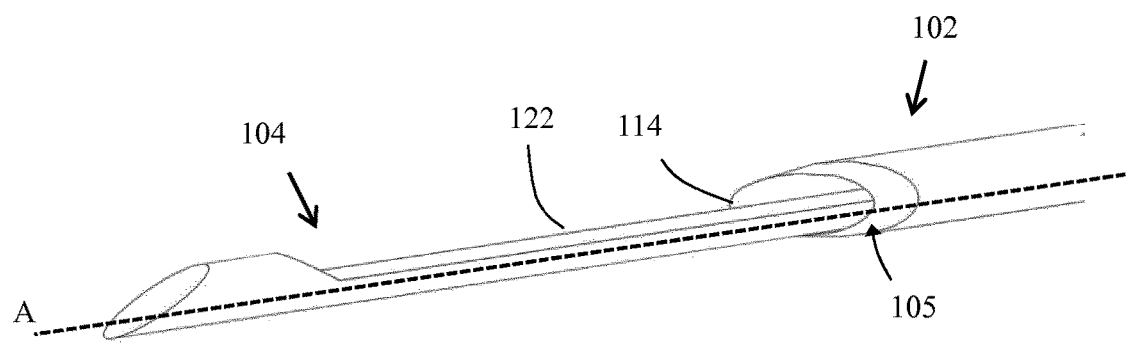
Figure 3C:
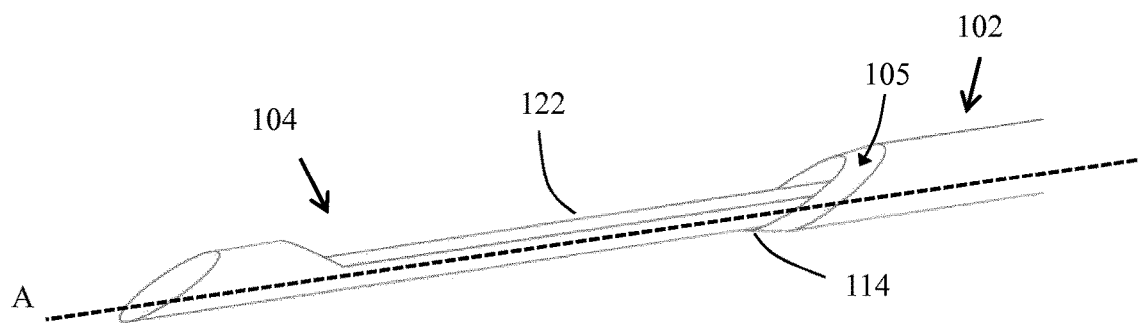

Examples of rotational alignment and misalignment between the stylet 104 and cannula 102 are shown in more detail in FIGS. 3a, 3b and 3c. As can be seen in these figures, the alignment means 126 (not visible in FIGS. 3a, 3b and 3c) may be arranged to align relative rotation about an axis A running along the length of the biopsy device 100 (e.g. along the length of the cannula body 106 or stylet body 116).

In some embodiments, the cannula 102 may have a preferred rotational cutting orientation and the stylet 103 may have a preferred rotational sampling orientation. The alignment means 126 may be arranged to align the cannula 102 and stylet 104 to align the preferred cutting orientation with the preferred sampling orientation. This may aid cutting of tissue and collection of a sample in the tissue sampling portion 122 of the stylet 104.

The preferred cutting orientation may be a preferred orientation of the cannula 102 when rotated about the longitudinal axis A as can be seen in FIGS. 3a to 3b. The preferred sampling orientation may similarly be a preferred orientation when the stylet 104 is rotated about the longitudinal axis A. The preferred cutting orientation of the cannula 104 may be determined by the position of the tissue piercing portion 114 of the cutting portion (e.g. by the shape of the cutting portion). For example, the tissue piercing portion 114 may be formed by a cutting tip extending from part of the distal end 108 of the cannula 102. Effective cutting may, for example, take place only where the tissue piercing portion 114 comes into first contact with tissue.

Similarly, the preferred sampling orientation of the stylet 104 may be determined by the shape and/or location of the tissue sampling portion 122. For example, the tissue sampling portion 122 may extend to only part of the stylet 104. For example, where the tissue sampling portion 122 is formed by a slotted or notched part of the stylet body 116, effective tissue sampling may only take place for tissue that is adjacent to the tissue sampling portion 122. For example, tissue that is located on the opposite side of the stylet body 116 may not be collected in the tissue sampling portion 122. The coupling mechanism may therefore be arranged to maintain relative rotation between the cannula 102 and stylet 104 such that the tissue piercing portion 114 and the sampling portion 122 coincide.

An example of desired rotational alignment between the stylet 104 and the cannula 102 can be seen in FIG. 3a. The tissue piercing portion 114 can be seen to coincide with the tissue sampling portion 122. The preferred cutting orientation is thus aligned with the preferred sampling orientation. When the cannula 102 slides over the stylet 104 to take a sample, the tissue that has entered the tissue sampling portion 122 will therefore be effectively cut by the tissue piercing portion 114.

An example of an undesired rotation alignment between the stylet 104 and the cannula 102 can be seen in FIGS. 3b and 3c. In these examples, the preferred orientation of the tissue piercing portion 114 and the tissue sampling portion 122 are misaligned. The tissue will not therefore be effectively cut at a location in which it has been received in the tissue sampling portion 122.

Figure 4A:
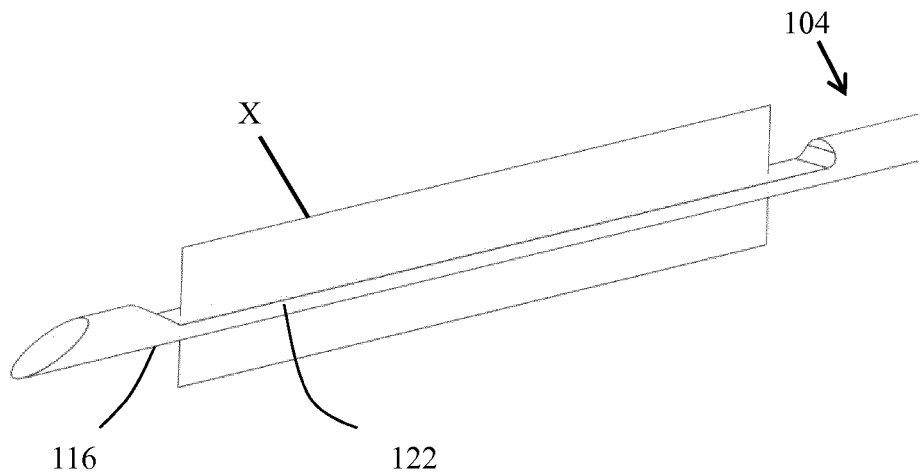

The alignment means may advantageously reduce or prevent relative rotation between the cannula 102 and stylet 104 that may otherwise occur during use of the biopsy device 100. For example, as the biopsy device 100 is advanced to a biopsy site, the distal ends of the cannula and stylet may flex in various planes as determined by the shape of the anatomy encountered. Because of its asymmetric shape (e.g. because of the shape and location of the tissue sampling portion 122) the stylet 104 may naturally tend to flex in a preferred plane X (as shown in FIG. 4a). The stylet 104 will tend to rotate so that this preferred plane of flexibility aligns with the direction in which the stylet is flexed during use as it moves through the anatomy. Contrary to this, the cannula 102 does not have such a preferred plane of flexibility. This may be because the cannula 102 is generally symmetrical in shape and construction about the longitudinal axis A. It will therefore tend to conform to the anatomical flexures without twisting or rotating. This difference in the rotational tendency of the cannula 102 and the stylet 104 may result in the misalignment shown in FIGS. 3b and 3c. The alignment means 126 is advantageously arranged to reduce or prevent this relative rotation and help ensure desired rotational alignment between the cannula 102 and stylet 104.

Figure 4B:
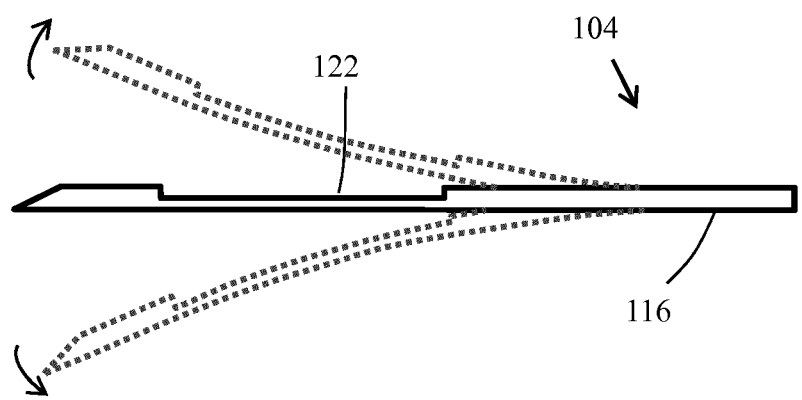

In some embodiments, the alignment means 126 may be arranged to align relative flexing between the cannula 102 and the stylet 102 as shown in FIGS. 4a and 4b. Relative flexing may include bending or curving of at least part of the stylet 104 while a corresponding part of the cannula 102 maintains a substantially straight configuration (as shown in FIG. 2b(i)). Relative flexing may also include bending or curving of at least part of the cannula 102 while a corresponding part of the stylet 104 maintains a substantially straight configuration (as shown in FIG. 2b(ii)). Relative flexing may also include flexing of both the stylet 104 and cannula 102 to a different degree to each other.

As already mentioned above, the stylet 104 may have a preferred plane of flexibility, labelled "X" in FIG. 4a. The stylet 104 may tend to naturally flex in this plane (as demonstrated in FIG. 4b) because of the shape and position of the tissue sampling portion 122. For example, where the tissue sampling portion 120 comprises a slot as shown in the described embodiment, the preferred plane of flexibility may be caused by the thinning of the material of the stylet 104 to form the slot. The alignment means 126 may be additionally or alternatively arranged to resist relative movement between the cannula 102 and stylet 104 in the preferred plane of flexibility. By resisting relative movement, the alignment means 126 is arranged to restrict the flexibility of the cannula 102 and the stylet 104 such that they flex to the same degree. This therefore prevents the stylet 104 from moving towards the cannula 102 (or vice versa) if the stylet flexes in its preferred plane of flexibility.

By resisting relative flexing between the stylet 104 and the cannula 102 in the preferred plane of flexibility, the risk of the tissue piercing portion 114 interfering with the tissue sampling portion 122 may be reduced. Without the alignment means 126 to reduce or prevent relative flexing, the stylet 104 may tend to flex such that the tissue piercing portion 114 moves towards or away from the tissue sampling portion 122. The alignment means 126 may therefore maintain the cutting efficiency and reduce the risk of the tissue piercing portion 114 gouging or damaging tissue in the tissue sampling portion 122 as the cannula 102 slides over the stylet 104 when taking a sample. This effect is demonstrated in FIG. 4c, in which the stylet 104 has flexed in its preferred plane of flexibility causing the tissue piercing portion 114 to contact tissue in the tissue sampling portion 122.

In some embodiments, the alignment means is arranged to align relative tilting and/or translational motion between the cannula 102 and the stylet 104.

The translational motion may include axial translation between the stylet 104 and the cannula 102 in a direction along the longitudinal axis A of the biopsy device. Translational motion may also include radial translation between the stylet 104 and the cannula 102 in a direction at least partly perpendicular to a longitudinal axis of the biopsy device (e.g. such that cannula and stylet are no longer concentrically aligned along axis A).

Axial translational misalignment may result in the cannula 102 and/or the stylet 104 being in the incorrect axial starting position for taking a tissue sample once the biopsy device has been positioned at the biopsy site. This may be caused by a relative shortening or lengthening of either of the cannula 102 and stylet 104 when the biopsy device is bent or twisted through tortuous anatomy. Axial misalignment may, for example, be the result of adding a flexible portion to the cannula body to improve its flexibility. This may cause it to change in length when bent through the anatomy during delivery to the biopsy site. If the length shortens, this may cause the cannula cutting portion 105 to align further proximally (e.g. toward the proximal end of the stylet) relative to the tissue sampling portion 122 than desired. If the length increases, this may cause the cannula cutting portion 105 to align further distally (e.g. toward the distal end of the stylet) relative to the tissue sampling portion 122 than desired.

The alignment means 126 may be arranged to resist or prevent any undesired relative axial translation until such a time that the relative sliding between the cannula 102 and stylet 104 is required to insert the stylet 104 into the biopsy site and to cut the surrounding tissue. In this embodiment, the preferred alignment between the cannula and stylet may be a relative axial alignment such that when the cannula 102 is advanced over the stylet 104 by a predefined amount the cannula covers the tissue sampling portion 122. The axial translation alignment is therefore separate to the relative sliding movement between the cannula 102 and stylet 104 caused by the control means during the collection of a sample.

The alignment means 126 may take a number of different forms such that it is adapted to align one or more of the different alignment modes described above. In some embodiments, the alignment means 126 comprises a coupling mechanism arranged to couple the stylet 104 and the cannula 102. In such an embodiment, the alignment means 126 is arranged to provide a mechanical coupling or engagement between the cannula 102 and the stylet 104 to maintain the preferred alignment between them. The coupling mechanism may therefore force the cannula 102 to adopt the same orientation as the stylet 104 by mechanically locking the two components together.

The coupling mechanism may comprise one or more raised portions of the cannula body 106 and corresponding recessed portions of the stylet body 116. The corresponding raised and recessed portions are arranged to engage with each other (e.g. they may interlock) to prevent or reduce relative movement between the cannula 102 and the stylet 104. The engagement between the raised portion(s) and the recessed portion(s) may, for example, resist relative rotation and/or flexing between the stylet 104 and the cannula 102.

The raised portions may extend into the lumen 112 so that they may engage with the recessed portions of the cannula 102. In some embodiments, the raised portions or the recessed portions, or both, may extend along the length of the stylet 104 or the cannula 102 (e.g. they may extend in a direction generally parallel to the longitudinal axis A). This may allow the coupling mechanism to allow sliding motion between the cannula 102 and stylet 104 along their respective length to allow a sample to be taken.

By providing a coupling mechanism formed by protrusions and recessed portions of the cannula and stylet an improved degree of alignment may be provided compared to any alignment provided by a close fit between the cannula 102 and stylet 104. This may be particularly important in the region of the tissue sampling portion 122 of the stylet 104 where the notch formed in the stylet body reduces the amount of surface contact between the stylet 104 and cannula 102. The coupling mechanism of this application may provide improved alignment even when the tissue sampling portion 122 of the stylet 102 is aligned with the cannula 104. In this configuration, relying on a close fit between an interior surface of the cannula body 106 and an exterior surface of stylet body may result in misalignment because of the incomplete surface contact between them.

FIGS. 5a-5g show an embodiment of the coupling mechanism. In this embodiment, the raised portions comprise a pair of ridges 128a, 128b (e.g. elongate protrusions) extending from the cannula body 106. The recessed portions comprise a pair of grooves 130a, 130b extending part way through the stylet body 116. The combination of the ridges 128a, 128b and the grooves 130a, 130b may resist or prevent both relative rotation and relative flexing between the cannula 102 and the stylet 104.

As can be seen in FIG. 5d, the ridges 128a, 128b forming the raised portions may be arranged to extend into the lumen 112 from an interior surface of the cannula body 106. The pair of ridges 128a, 128b may be disposed on opposite sides of the interior of the cannula body 106 (i.e. on opposite sides of the circumference of the interior surface of the cannula body which defines the lumen 112) as shown in FIG. 5b. The grooves 130a, 130b may be formed in corresponding opposite sides of the stylet body 116. In the described embodiment, two pairs of grooves and ridges are provided to help give a secure coupling between the cannula 102 and the stylet 104. In other embodiments, other numbers of grooves and ridges may be provided. For example, four pairs of grooves and ridges may be provided. Furthermore, the pairs of grooves and ridges may be equally spaced around the circumference of the stylet body 116 and the cannula body 106 to aid coupling. In other embodiments, the grooves and ridges may be unequally spaced.

In some embodiments, one or all of the recessed portions may define a first abutment surface (two of which are shown in the figures, labelled 132a, 132b) and one or all of the raised portions may define a second abutment surface (two of which are shown in the figures, labelled 134a, 134b). The abutment surfaces 132a, 132b, 134a, 134b may be arranged such that contact between them resists relative movement between the stylet 104 and cannula 102 in the preferred plane of flexibility of the stylet. This type of coupling mechanism may therefore prevent or reduce relative rotation and relative flexing of the cannula and stylet at the same time. As can be seen in FIGS. 5a-5g, the abutment surfaces may be arranged to extend in a plane substantially perpendicular to the plane of preferred flexibility of the stylet 104. This may help to resist relative movement between the cannula 102 and stylet 104 in the preferred plane of flexibility. The engagement of the abutment surfaces may, for example, force the flexing of the cannula 102 to follow that of the style 104 if the stylet flexes in the preferred plane during use.

In other embodiments, the abutment surfaces 132a, 132b, 134a, 134b may be angled relative to the plane of preferred flexibility of the stylet 104. In such an embodiment, the abutment surfaces may extend in a plane having at least a component substantially perpendicular to the plane of preferred flexibility of the stylet 104 so as to resist relative movement of the stylet and cannula in that plane.

The embodiment shown in FIGS. 5a-5g is only one example of the shape and configuration of the raised and recessed portions. In other embodiments, the skilled person would understand that the shape and arrangement of the raised and recessed portions may be adapted to provide effective alignment of any one or more of the different modes of alignment described above. For example, in the embodiment of FIGS. 5a-5g the raised and recessed portions may be integral with the body of the stylet or cannula. In other embodiments, they may be formed by separate components attached to the cannula or stylet body.

Figure 6A:
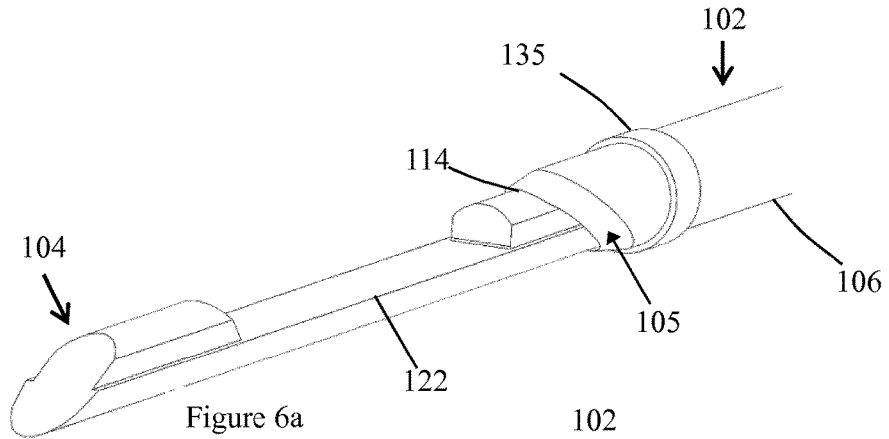
FIGS. 6a to 6c show relative movement of a cannula and stylet having a coupling mechanism according to another embodiment of a coupling mechanism used to align a cannula and a stylet of a biopsy device.
Figure 6B:
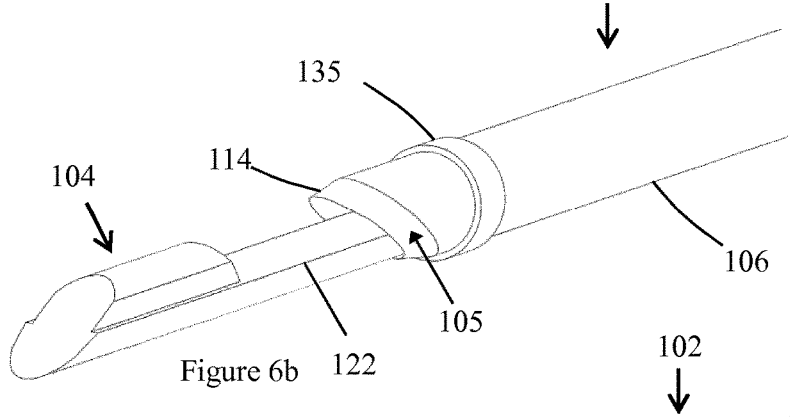
Figure 6C:
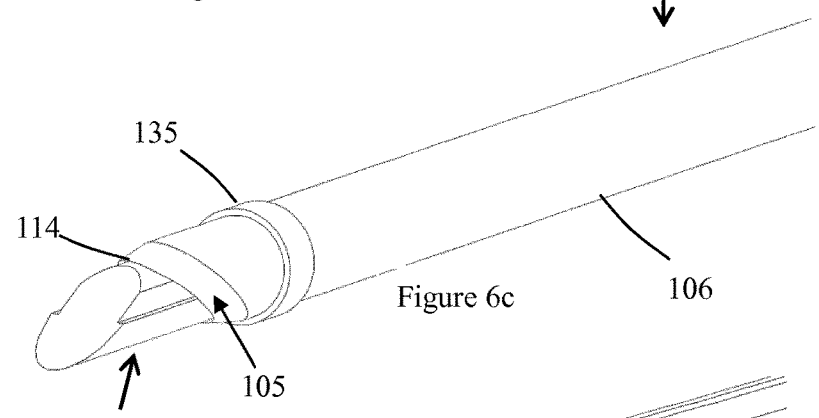
Figure 6D:
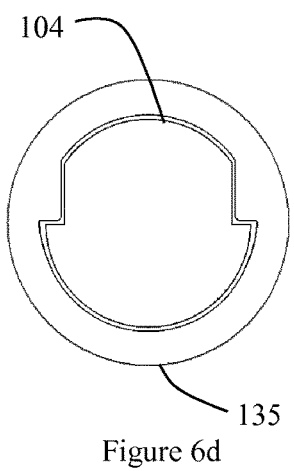
FIG. 6d shows a cross section view through the coupling mechanism of the embodiment shown in FIGS. 6a to 6c.
Figure 6E:
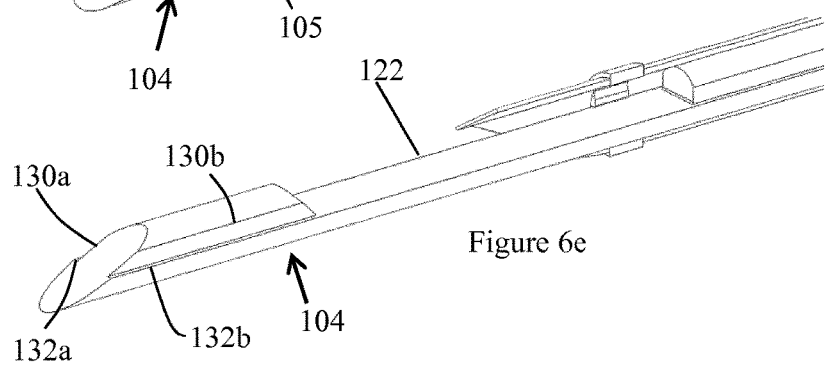
FIG. 6e shows a partial cut away view of the coupling mechanism of the embodiment shown in FIGS. 6a to 6c.

Another embodiment of the mechanical coupling mechanism acting between the stylet 104 and the cannula 102 is shown in FIGS. 6a, 6b, 6c, 6d and 6e. Reference numerals corresponding to those of FIGS. 5a-5g have been used for ease of explanation. FIG. 6a shows the distal end of the stylet 104 extended from the distal end of the cannula 102. FIGS. 6b and 6c show the cannula 102 being advanced by varying amounts over the stylet 104. FIG. 6d shows a cross section through an alignment insert 135 with raised portions when the stylet 104 and the cannula 102 are aligned as per FIG. 6a, and FIG. 6e shows a cut away view through the body 106 of the cannula when the stylet 104 and the cannula 102 are aligned as per FIG. 6b. In the embodiment shown in FIGS. 6a-6e the mechanical coupling mechanism is formed by a pair of grooves 130a, 130b provided in the stylet body as described above in relation to FIGS. 5a-5g. The grooves each form a respective abutment surface 132a, 132b to engage with a corresponding surface on the cannula 102. In this embodiment, the abutment surfaces 132a, 132b are aligned with the tissue sampling portion 122 so that a surface of the tissue sampling portion forms part of the abutment surfaces 132a, 132b. This may help to aid alignment even when the cannula distal end is level with the tissue sampling portion 122 (e.g. in FIG. 6b). In other embodiments, the grooves may be provided at any suitable alternative or additional position around the circumference of the stylet body.

The mechanical coupling mechanism further comprises a corresponding pair of raised portions provided on the cannula to engage with the grooves 130a, 130b of the stylet 104. In this embodiment, the raised portions are each formed on an insert 135 that can be welded or otherwise joined immediately adjacent or close to the cutting portion 105 of the cannula 102.

Figure 7A:
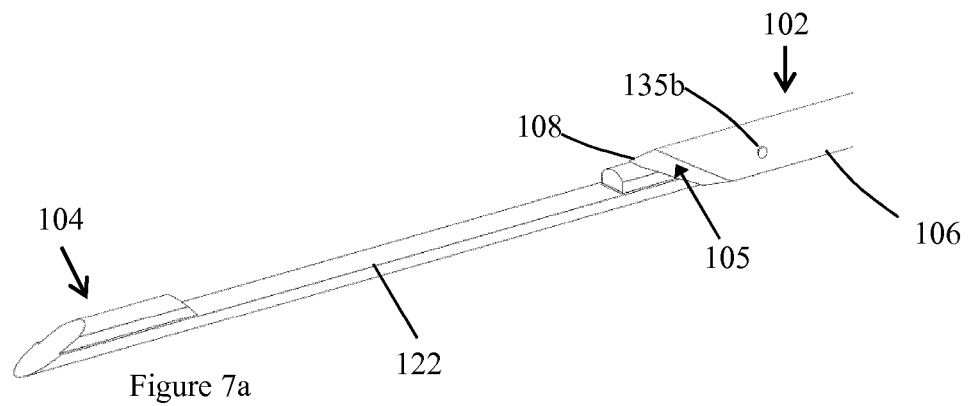
FIGS. 7a to 7c show relative movement of a cannula and stylet having a coupling mechanism according to another embodiment.
Figure 7B:
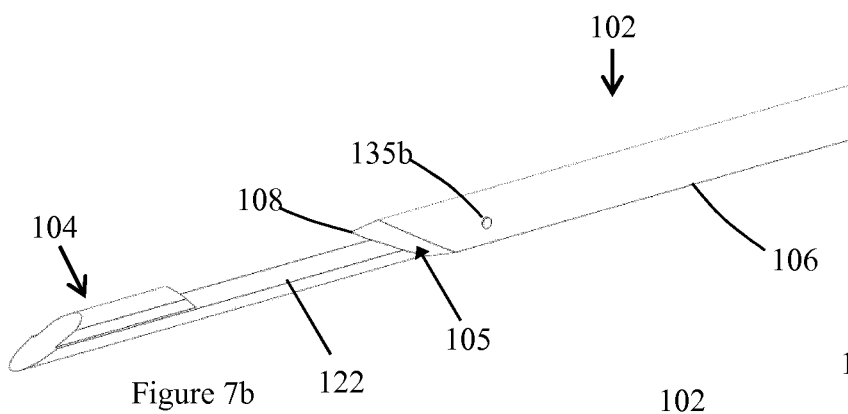
Figure 7C:
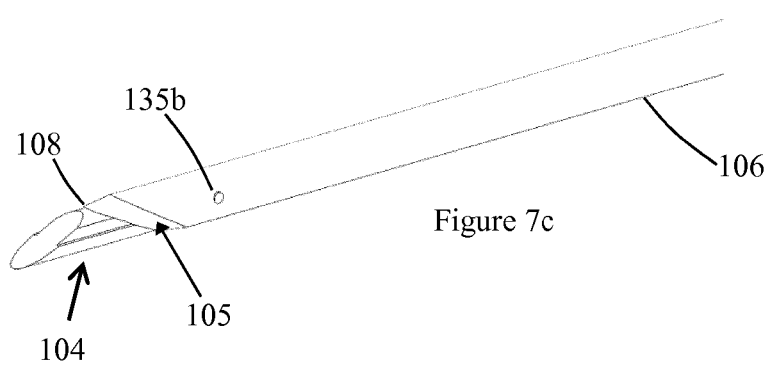
Figure 7D:
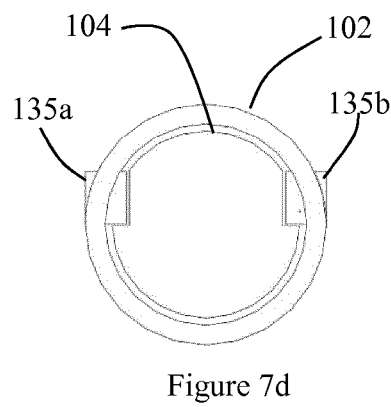
FIG. 7d shows a cross section view through the coupling mechanism of the embodiment shown in FIGS. 7a to 7c.
Figure 7E:
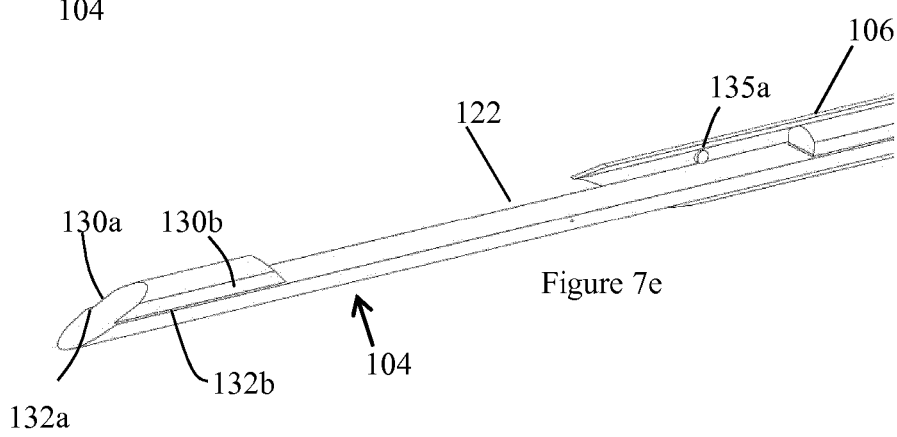
FIG. 7e shows a partial cut away view of the coupling mechanism of the embodiment shown in FIGS. 7a to 7c.
Figure 8A:
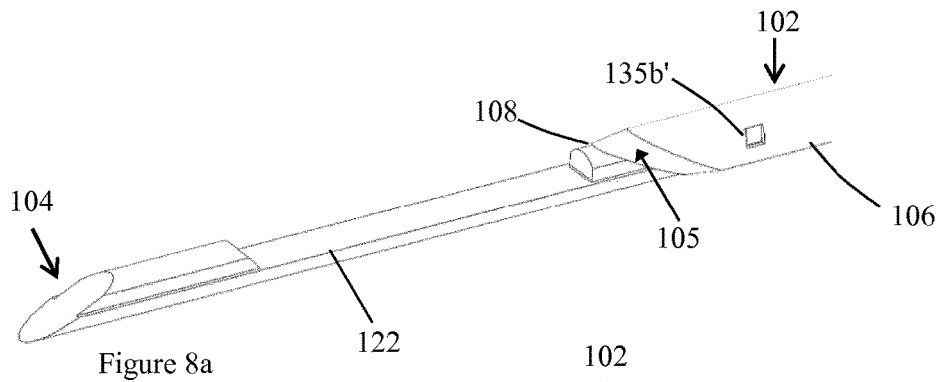
FIGS. 8a to 8c show relative movement of a cannula and stylet having a coupling mechanism according to another embodiment.
Figure 8B:
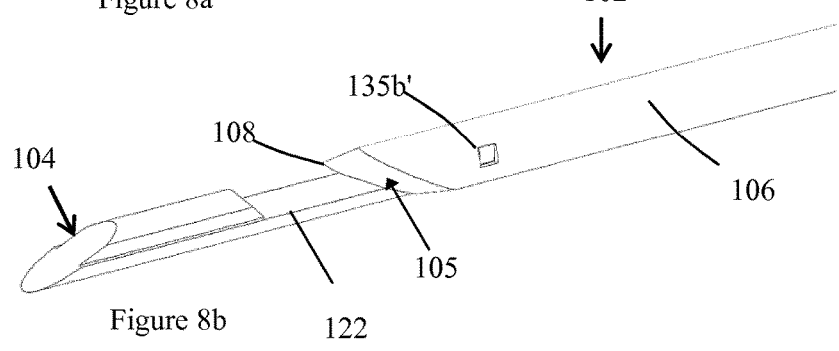
Figure 8C:
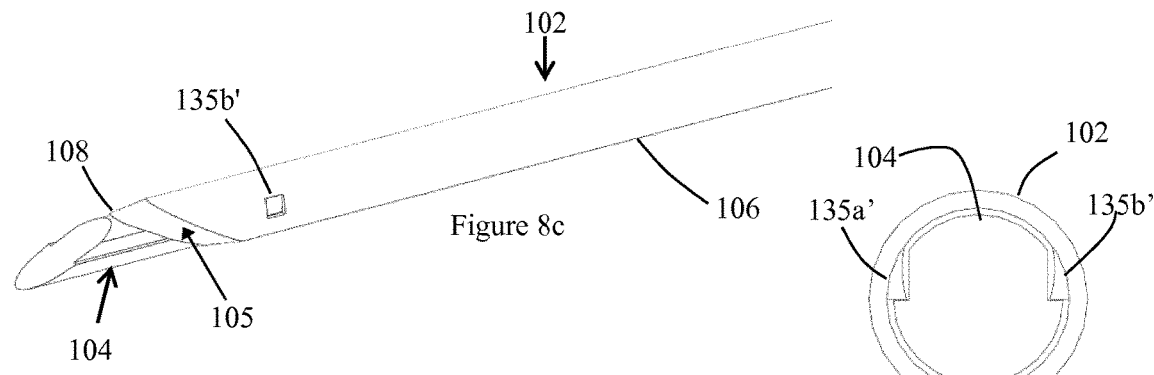
Figure 8D:
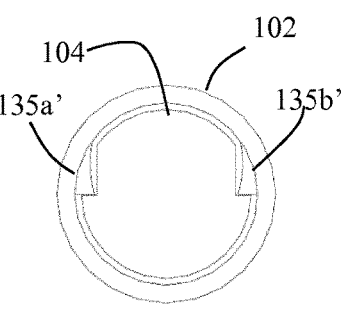
FIG. 8d shows a cross section view through the coupling mechanism of the embodiment shown in FIGS. 8a to 8c.
Figure 8E:
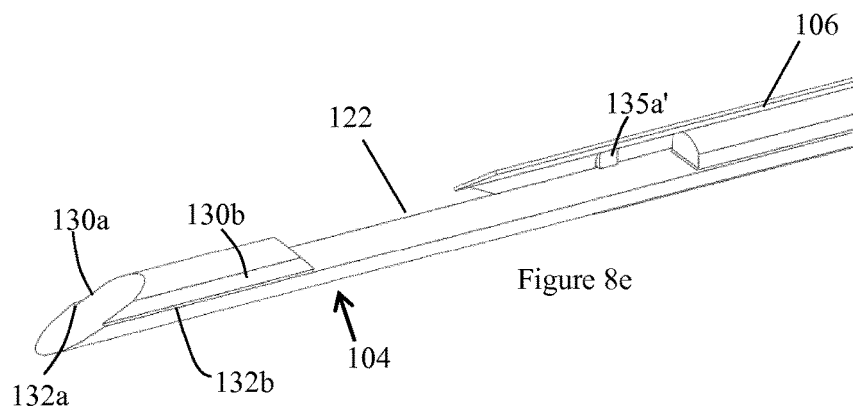
FIG. 8e shows a partial cut away view of the coupling mechanism of the embodiment shown in FIGS. 8a to 8c.

Another embodiment of the mechanical coupling mechanism is shown in FIGS. 7a-7e. These Figures show views of the biopsy device corresponding to the views shown in FIGS. 6a-6e. FIG. 7d shows a cross section immediately distal to the alignment pins 135a, 135b when the stylet 104 and the cannula 102 are aligned as per FIG. 7a, The embodiment of FIGS. 7a-7e includes a stylet 104 similar to that shown in FIGS. 6a-6e. In the embodiment of FIGS. 7a-7e the raised portions of the mechanical coupling mechanism provided on the cannula 102 are each formed from a pin 135a, 135b extending through the cannula body 106. In this embodiment, the pins 135a, 135b are inserted into a through hole extending through the cannula body 106. In other embodiments, the pins may be inserted into a blind hole extending into the wall of the cannula body 106. In the embodiment of FIGS. 7a-7e a pair of pins 135a, 135b are shown positioned near to the distal end of the cannula 102. In other embodiments, any other suitable number of pins may be provided around the circumference of the cannula body 106 to engage with additional grooves provided on the stylet 104. In yet other embodiments, additional or alternative pins may be provided at positions spaced apart along the length of the cannula body 106. Such pins may engage with grooves on the stylet 102 which extend further along the body of the stylet 102 towards the stylet proximal end. This may provide coupling of the cannula 102 and stylet 104 along a greater portion of their respective lengths.

Another embodiment of the mechanical coupling mechanism is shown in FIGS. 8a-8e. These Figures show views of the biopsy device corresponding to the views shown in FIGS. 6a-6e. The embodiment of FIGS. 8a-8e again includes a stylet 104 similar to that shown in FIGS. 6a-6e. In the embodiment of FIGS. 8a-8e the raised portions of the mechanical coupling mechanism provided on the cannula 102 are each formed from a protrusion formed by a dimple 135a', 135b' pressed into the outer surface of the cannula body which causes a corresponding protrusion on the inner surface of the cannula body (e.g. protruding into the lumen). In some embodiments, forming of the dimple may be facilitated by selectively removing material at the location of the dimple, for example by laser-cutting a U-shaped pattern through the wall of the cannula body, prior to pressing of the dimple.

Figure 9A:
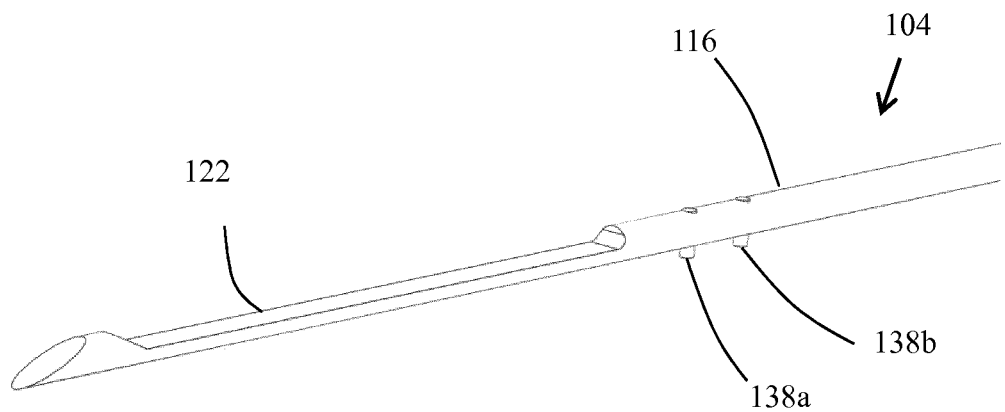
FIGS. 9a to 9c show another embodiment of a coupling mechanism used to align a cannula and stylet of a biopsy device.
Figure 9B:
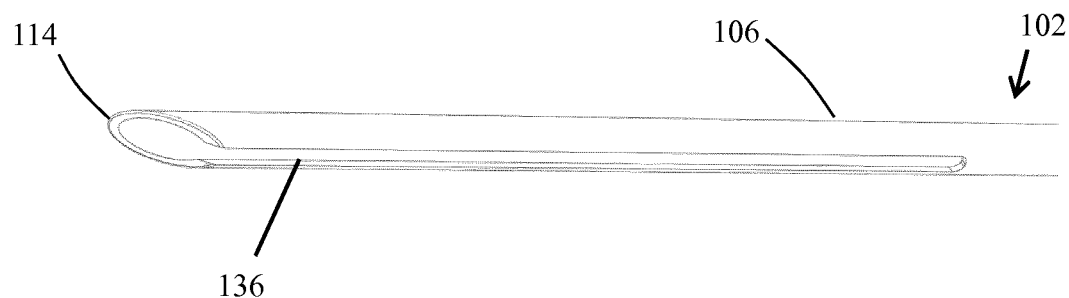

In other embodiments, the recessed portion and the raised portion forming the mechanical coupling may be reversed such that the recessed portion is provided on the cannula 102 rather than the stylet 104, and the raised portion is provided on the stylet 104 rather than the cannula 102. For example, the embodiments shown in the Figures include male features with corresponding female features on the stylet. This configuration may allow the biopsy device to be more easily manufactured. However, in other embodiments, the female features may be provided on the cannula and the corresponding male features provided on the stylet (e.g. as shown in FIGS. 9a and 9b).

In yet other embodiments, each of the cannula 102 and the stylet 104 may have any number of corresponding recessed portions and raised portions. For example, in some embodiments, only one recessed portion and raised portion may be provided. In some embodiments, the recessed portion and raised portions may preferably be provided at or near the distal end of the cannula and stylet. In other embodiments, they may additionally or alternatively be provided at other points along the length of the cannula and stylet.

Figure 9C:
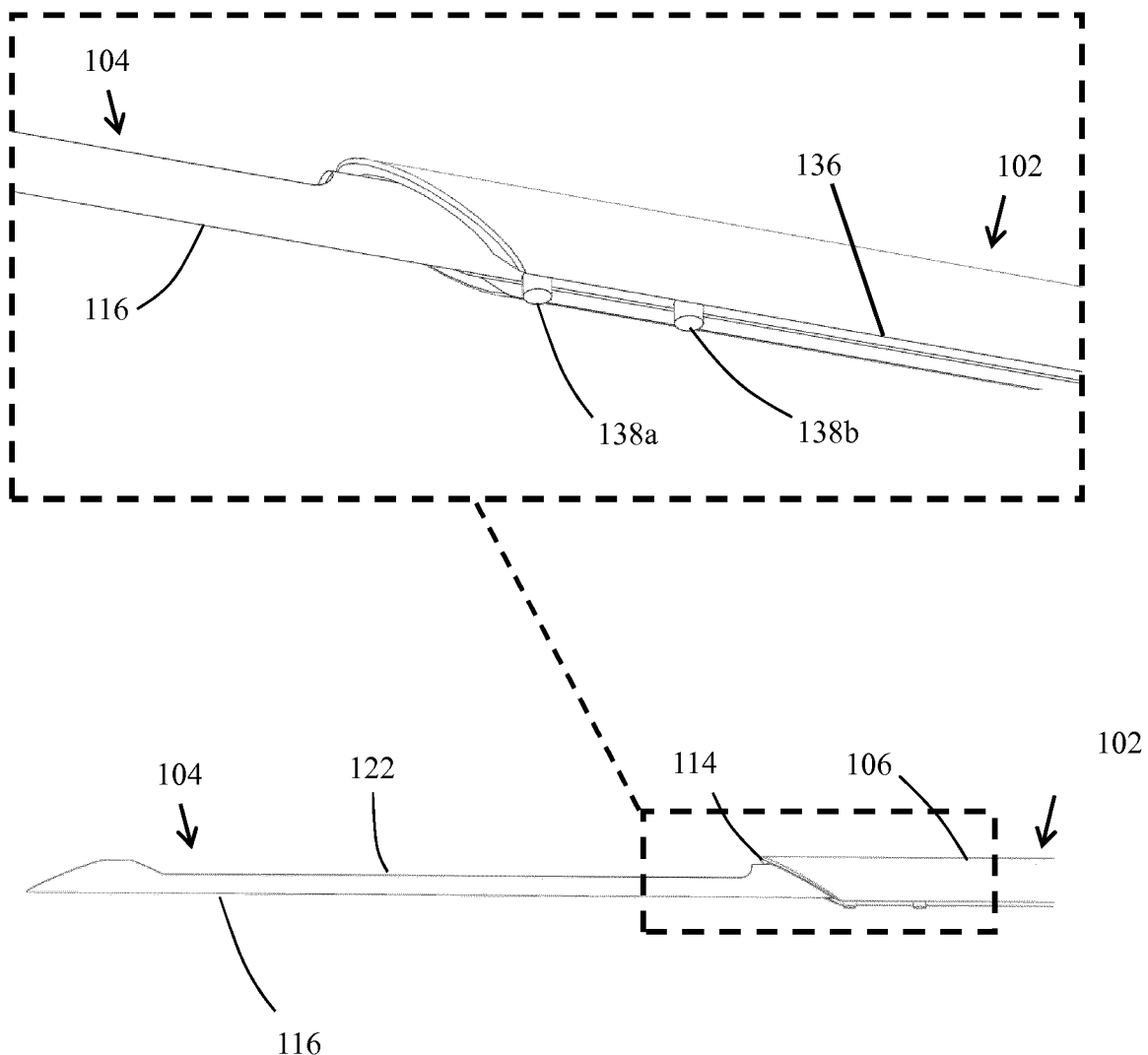

In some embodiments, the raised portion and the recessed portion may take other forms that provide a mechanical coupling between the cannula 102 and stylet 104. In one embodiment, as shown in FIGS. 9a, 9b and 9c, the recessed portion may comprise a slot 136 extending through the body 106 of the cannula 102 (or part way through the body 106 in other embodiments). The corresponding raised portion may comprise one or more pins 138a, 138b (two of which are shown in the Figures), extending from the body 116 of the stylet 104, which may be received in the slot. The pins 138a, 138b may have a generally circular cross section as shown in FIG. 9a, but in other embodiments may have other suitable shapes or profiles. In the embodiment shown in FIG. 9a, the pins are formed by inserts fitted into the stylet body 116, and may for example be inserted into holes formed in or through the stylet body 116. In yet other embodiments, the pins may be attached or machined into the stylet body 116. They may, for example, be separate components, or may be integral with the stylet body 116. In yet other embodiments, any number of slots may be provided in the cannula 102 rather than the single slot 136 shown in FIG. 9b. Each slot may have a respective set of one or more pins formed on the stylet 104. For example, in some embodiments, a pair of opposing slots may be formed on opposite sides of the cannula 102. In yet other embodiments, the arrangement of the slot(s) and pin(s) may be reversed such that the slot(s) are provided on the stylet 104 and the pin(s) may be provided on the cannula 102.

In some embodiments, the arrangement of the recessed portion and raised portion may additionally or alternatively act to prevent or reduce axial misalignment of the cannula 102 and stylet 104. The recessed portion may be arranged to restrict the range of axial translation of the raised portion, thereby maintaining the cannula 102 and the stylet 104 in a preferred axial alignment.

In the embodiment shown in FIGS. 5a to 5g, the grooves 130a, 130b each comprise a proximal end stop surface 133a, 133b arranged to engage with a proximal end stop surface 135a, 135b of the ridges 128a, 128b. Engagement of the proximal end stop surfaces may restrict the range of axial translation between the cannula and stylet in a direction toward the proximal end of the cannula 102. In other embodiments, one or both of the grooves 130a, 130b may each comprise a distal end stop surface arranged to engage with a distal end stop surface of the ridges 128a, 128b. Engagement of the distal end stop surfaces may restrict the range of axial translation between the cannula and stylet in a direction toward the distal end of the cannula.

In the embodiment shown in FIGS. 9a and 9b, the closed proximal end of the slot 136 shown in FIG. 9b may form a proximal stop surface to restrict the range of movement of the cannula 102 relative to the one or more pins 138a, 138b in the proximal direction (e.g. toward the proximal end of the stylet). In other embodiments, the distal end of the slot 136 may alternatively or additionally be closed to form a distal stop surface. This may restrict the range of movement of the cannula 102 relative to the one or more pins 138a, 138b in the distal direction (e.g. towards the distal end of the stylet).

In yet other embodiments, the coupling mechanism may comprise a portion (or portions) of the body of the stylet 104 and a portion (or portions) of the lumen of the cannula 104 each having a corresponding non-circular cross section. These non-circular portions may be any suitable shape which may resist or prevent relative rotation (or flexing) between the cannula 102 and stylet 104. For example, the non-circular portion of the lumen and stylet body may comprise an elliptical, square or rectangular shape in cross section, or may comprise any other more complex, non-circular shape. The non-circular portion(s) may be located along any part of the length of the cannula 102 and the stylet 104, or along the entire length of the cannula 102 and stylet 104. In some embodiments, the non-circular portion may be formed by the recessed portion and raised portion described above, or may be provided additionally or alternatively to the raised and recessed portions. The engagement between the non-circular portions of the cannula body 106 and the stylet body 114 may aid resistance to relative rotation between them to help aid alignment.

In some embodiments, the coupling mechanism may be disposed at or near the cannula distal end 108 and the stylet distal end 118. Near to the distal end may include being closer to the cannula or stylet distal end compared to the proximal end. In some embodiments, the coupling mechanism may be disposed within a distal region of the cannula and/or a distal region of the stylet. The distal region(s) may include a portion of the cannula or stylet extending away from the distal tip of the cannula and stylet, and in the case of the stylet include the tissue sampling portion. The distal region(s) may be opposite to proximal regions of the cannula and the stylet at which the control means may be provided to couple the cannula and stylet as described above. The cannula and stylet may each further comprise an intermediate region extending between the respective distal region and proximal regions. The coupling mechanism may be disposed within the distal region of the cannula and/or the stylet such that it acts directly on the cannula distal end 108 and the stylet distal end 118 to maintain alignment between them.

The distal region of the cannula may extend from the cannula distal end a distance of up to or equal to 25% of the distance between the cannula distal end and the cannula proximal end. The cannula distal region may therefore be formed by a length of the cannula body measuring no more than approximately 25% of its total length. Similarly, the distal region of the stylet may extend from the stylet distal end a distance of up to or equal to 25% of the distance between the stylet distal end and the stylet proximal end. The stylet distal region may therefore be formed by a length of the stylet body measuring no more than approximately 25% of its total length. By positioning the coupling mechanism within this region of the total length of the biopsy device it may provide suitable alignment of the cannula and stylet distal ends.

By "up to or equal to" 25% we mean up to or approximately equal to 25% i.e. a level of tolerance may be provided on the upper limit of 25% so long as the same level of alignment is provided.

In some embodiments, the distal region of the cannula may extend from the cannula distal end a distance of up to or equal to 50 mm. Similarly, the distal region of the stylet may extend from the stylet distal end a distance of up to or equal to 50 mm. This may provide further improved alignment of the cannula and stylet distal ends. For comparison, in this embodiment, the tissue sampling portion may extend along the stylet body such that its proximal end is about 25 mm from the distal end of the stylet, and may itself be about 20 mm in length along the stylet body. The overall total length of the cannula and stylet may be in excess of 1 m. Other lengths of the device and tissue sampling portion may be possible.

By "up to or equal to" 50 mm we similarly mean up to or approximately equal to 50 mm i.e. a level of tolerance may be provided on the upper limit of 50 mm so long as the same level of alignment is provided.

In some embodiments, the stylet distal region may comprise a region of the stylet extending between the stylet distal end and a distal end of the tissue sampling portion. This may provide improved alignment between the tissue sampling portion and the cannula to reduce the risk of gauging collected tissue.

In embodiments where the coupling mechanism is disposed within the cannula or stylet distal regions it may be only partly disposed within those regions. It may also extend further along the length of the cannula and/or the stylet to provide further relative alignment improvement.

In some embodiments, the ridges 128a, 128b or the grooves 130a, 130b, or both, may extend from at (or near) the distal end of the stylet 104 and/or the cannula 102. In other embodiments, the slot 136 or non-circular portions described above may be arranged at or near the respective cannula distal end 108 and stylet distal end 118. This may help the coupling mechanism 126 to align the distal ends of the stylet 104 and cannula 102, and may more effectively align the cutting portion 105 and the tissue sampling portion 122. In other embodiments, the coupling mechanism may be provided along any part or along all of the length of the cannula 102 and stylet 104.

In other embodiments, the alignment means 126 may comprise a biasing mechanism arranged to bias the flexing of the cannula 102 in a plane corresponding to the preferred plane of flexibility of the stylet 104. The biasing mechanism may be provided in addition or alternatively to the coupling mechanism described above. The biasing mechanism may encourage the cannula 102 to follow the orientation of the stylet 104 to aid alignment.

The biasing mechanism may be arranged to match the preferred direction of flexibility of the cannula 102 with that of the stylet 104. As described above, the stylet 104 may have a plane of flexibility X in which it naturally tends to flex because of the shape of the stylet 104 or the material it is made from. By matching the preferred plane of flexibility of the cannula 102 and the stylet 104, the risk of them becoming misaligned during use of the biopsy device 100 may be reduced.

The biasing mechanism may comprise at least one flexibility control portion of the cannula body 106 having a different flexibility to the rest of the cannula body 106. In some embodiments, the flexibility control portion may comprise a weakened portion of the cannula body 106 having an increased flexibility to the rest of the cannula body 106. For example, in the embodiment shown in FIGS. 10a and 10b, and 11a, 11b and 11c the weakened portion may comprise one or more slots 140 (only one of which is labelled in the figures) in the cannula body 106. In other embodiments, the weakened portion may comprise a reduced thickness portion of the cannula body 106, or a portion of the cannula body 106 comprising a material having a different flexibility compared to adjacent parts of the cannula body 106. In yet other embodiments, the flexibility control portion may comprise a portion of the cannula body 106 having a reduced flexibility compared to the rest of the cannula body 106. For example, the flexibility control portion may comprise a portion of the cannula body 106 having an increased thickness, or may comprise a portion of the cannula body 106 being made from a stiffer material, or may comprise a separate stiffening member attached to the cannula body. In yet other embodiments, the biasing mechanism may comprise one or more springs or deformable members arranged to control the flexibility of the cannula 102.

The size, shape and/or position of the flexibility control portion may be chosen to control the flexibility of the cannula 102 such that it is matched to that of the stylet 104. For example, the slots 140 or weakened portion forming the biasing mechanism are disposed on the cannula body such that flexibility of the cannula is increased in a plane corresponding to a preferred plane of flexibility of the stylet 104.

Figure 10A:
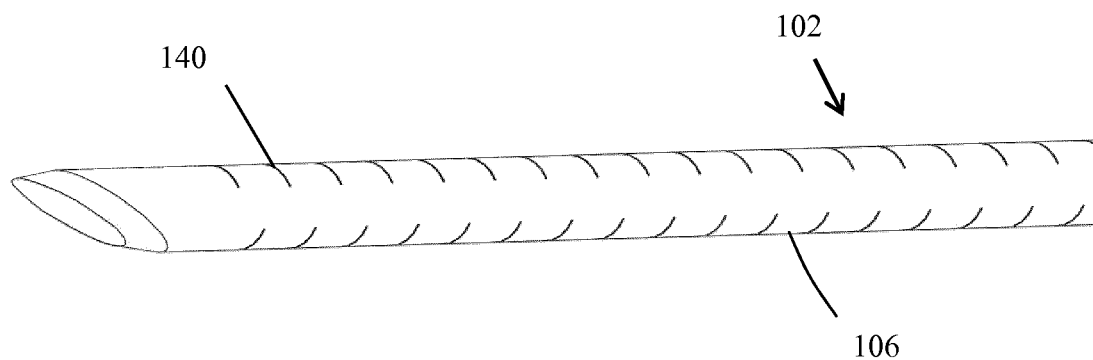
FIGS. 10a and 10b show an embodiment of a biasing mechanism used to align the cannula and stylet of a biopsy device.

The flexibility control portion may comprise at least a first and second flexibility control portion disposed on opposing sides of the cannula. This may provide sufficient flexibility to aid rotational alignment of the cannula 102 and stylet 104 as described above. For example, as can be seen in FIG. 10a, the flexibility portion may be formed by a first set of slots and a second set of slots, the first and second set of slots may be disposed on opposing sides of the cannula body 106 (e.g. they may be opposite each other around the circumference of the cannula body 106). The slots 140 may therefore be arranged to weaken the cannula body in a plane corresponding to the preferred plane of flexibility of the stylet 104.

The flexibility control portion of the cannula may be arranged to overlap or coincide with the sampling portion 122 when the cannula distal end 108 and stylet distal end 118 are longitudinally aligned. For example, in the described embodiment, the slots 140 forming the flexibility control portion may be arranged to overlap the sampling portion 122 when the cannula distal end 108 and the stylet distal end 118 are longitudinally aligned. This means that the flexibility control portion and the tissue sampling portion 122 overlap when the distal end of the stylet 104 is approximately flush with the distal end of the cannula 102. This position of the flexibility control portion may help allow the biasing mechanism to control the flexibility of the cannula 102 to reduce misalignment between the cutting portion 105 and the tissue sampling portion 122. In other embodiments, the flexibility control portion(s) may be provided at any position along the length of the cannula body 106.

The flexibility control portion may in some embodiments be provided only on the cannula 102 and not on the stylet 104. For example, in the described embodiment, the slots 140 forming the flexibility control portion are provided only in the cannula body 106 and are not present on the stylet 104. This allows the slots 140 to match the flexibility of the cannula 102 relative to the existing flexibility of the stylet 104. As the stylet 104 may already have a natural preferred direction of flexibility no further biasing means is required to control its flexibility. Any additional slots or other flexibility control portions provided on the stylet 104 may therefore unnecessarily compromise its structural strength while providing little improvement in alignment. In other embodiments, a flexibility control portion may however be provided on both the stylet 104 and the cannula 102.

Figure 4C:
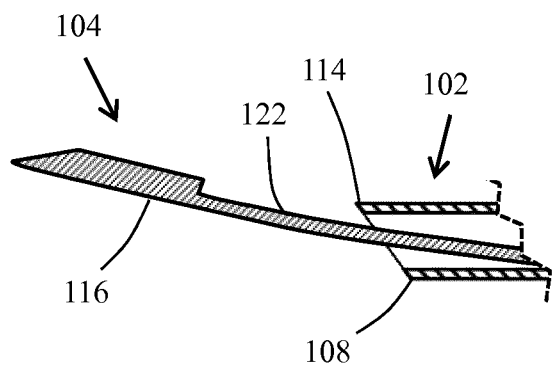
Figure 5E:
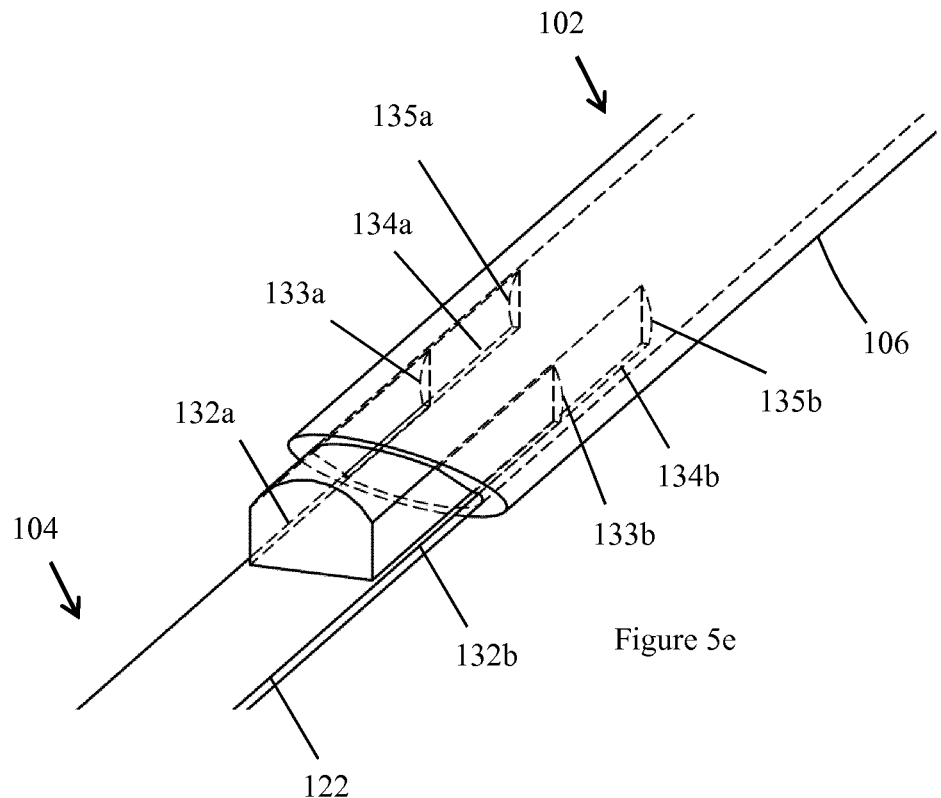
Figure 5F:
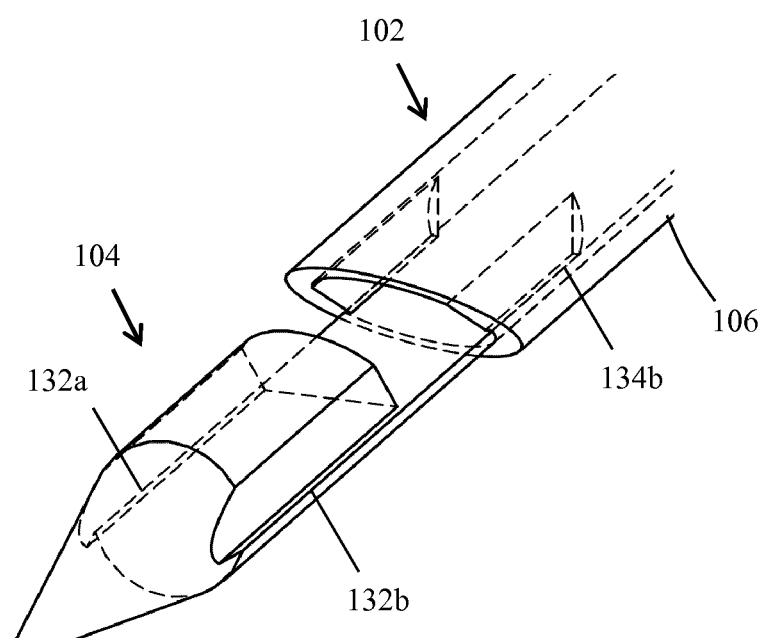
Figure 5G:
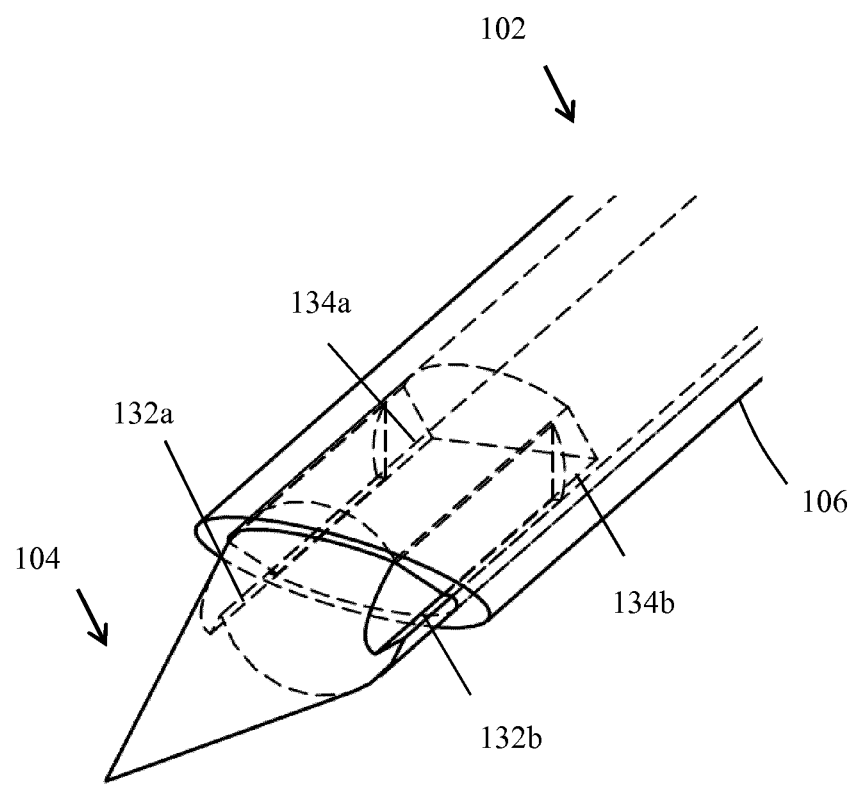
Figure 10B:
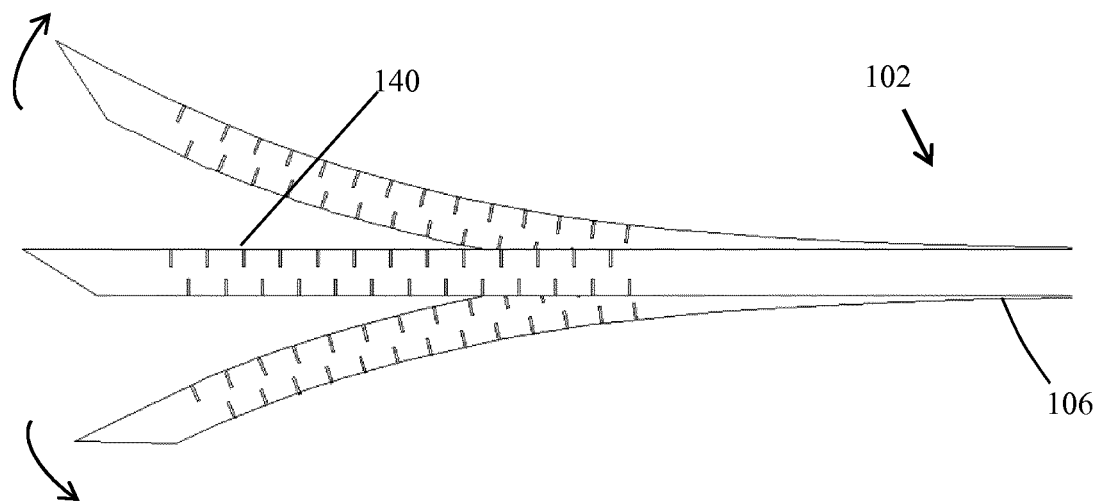

In some embodiments, the biasing mechanism may be arranged to prevent or minimise flexing of the cannula towards the stylet such that the tissue piercing portion 114 is prevented or discouraged from moving towards the tissue sampling portion 122 (i.e. the biasing mechanism may resist flexing of the cannula in one of the two possible flexure directions in the preferred plane of flexibility of the cannula shown in FIG. 10b and as shown in FIG. 4c). This may allow the alignment means 126 to prevent or minimise the risk of gouging of tissue in the tissue receiving sampling portion 122 by the tissue piercing portion 114.

Figure 11A:
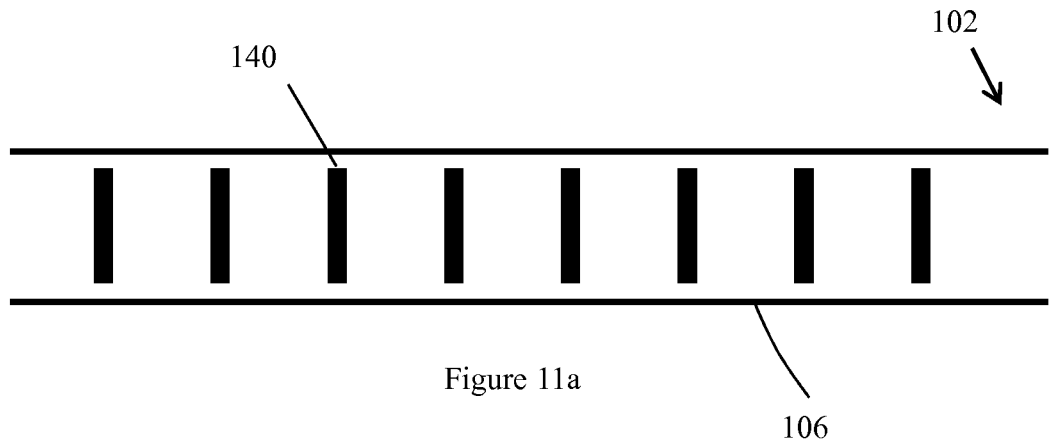
FIGS. 11a to 11c show another embodiment of a biasing means used to align the cannula and stylet of a biopsy device.
Figure 11B:
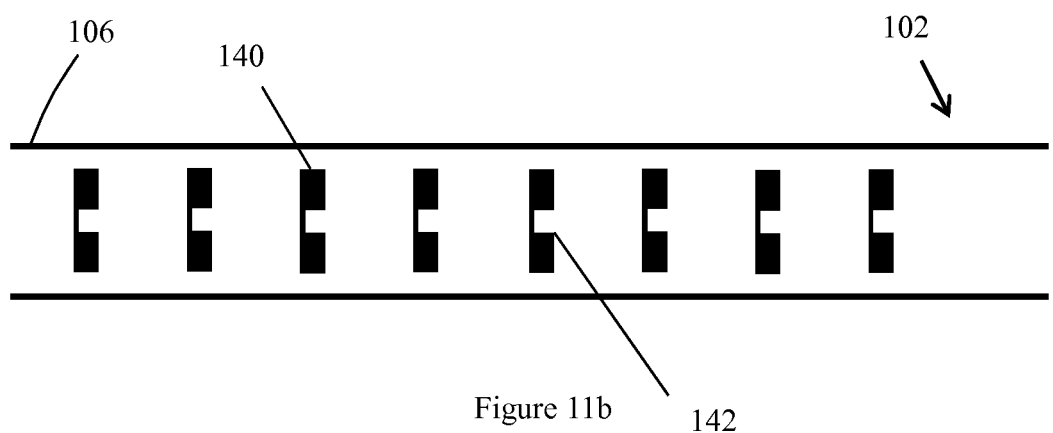
Figure 11C:
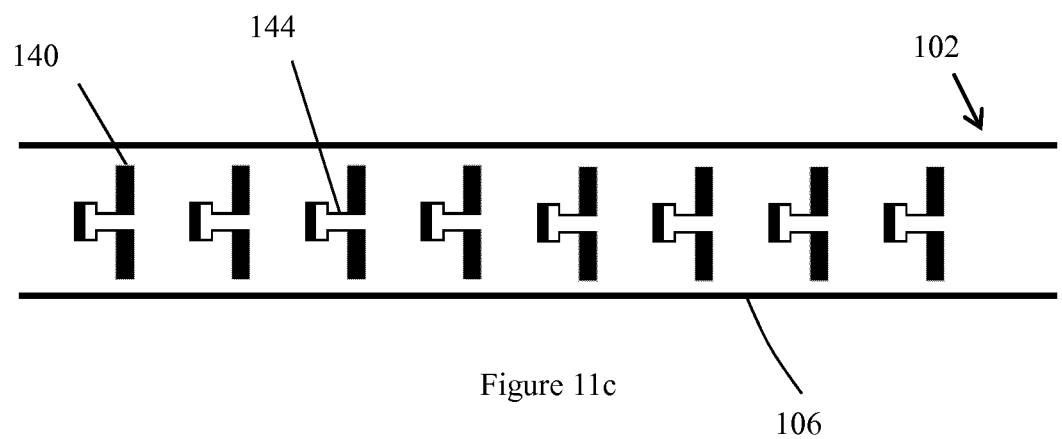

In one embodiment, as shown in FIGS. 11b and 11c, at least one of the first and second sets of slots may comprise at least one stop member arranged to resist flexibility of the cannula in a first direction. In the described embodiment, the first set of slots are provided with a first set of one or more stop members (one of which is labelled 142 in the FIG. 11b arranged to allow the first set of slots to expand in size, but resist any contraction in size. The first set of stop members 142 may therefore prevent or resist flexing of the cannula in a first direction (e.g. out of the page in FIG. 11b) and allow flexing of the cannula in a second direction (e.g. into the page in FIG. 11b). The first set of stop members 142 may be provided on the opposite side of the cannula 102 to the tissue piercing portion 114 so as to restrict its movement towards the tissue sampling portion 122, and may allow its movement away from the tissue sampling portion 122.

The second set of slots are provided with a second set of stop members (one of which is labelled 144 in the FIG. 11c). The second set of stop members 144 are arranged to resist or prevent expansion of the second set of slots, but allow contraction of the slots (e.g. allow a certain extent of contraction). The second set of stop members 144 may therefore allow flexing of the cannula in the first direction (e.g. out of the page in FIG. 11c) and prevent or resist flexing of the cannula in the second direction (e.g. into the page in FIG. 11c). This may therefore allow the biasing mechanism to prevent or resist movement of the cannula and the stylet in a direction in which the tissue piercing portion 114 would move towards the tissue sampling portion 122. The second set of stop members 144 may be provided on the same side of the cannula 102 to the tissue piercing portion 114 so as to restrict its movement toward the tissue sampling portion 122, and may allow its movement away from the tissue sampling portion 122.

The slot members on either side of the cannula 102 may be arranged such that they have different types of stop members (e.g. either those of FIG. 11b or 11c) on opposite sides of the cannula 102. In some embodiments, the first set of slots may be provided with one or more first stop members 142 (e.g. as shown in FIG. 11b), while the second set of slots on the opposite side of the cannula are provided with no stop members (e.g. as shown in FIG. 11a). In yet other embodiments, the second set of slots may be provided with one or more of the second stop members 144 (as shown in FIG. 11c) while the first set of slots is provided with no stop members (as shown in FIG. 11a). Each of these arrangements may provide the desired resistance of movement of the cannula 102 and the stylet 104 in a direction in which the tissue piercing portion 114 would move towards the tissue sampling portion 122.

The various embodiments of the alignment means 126 described above may provide one or a combination of more than one of the different alignment modes between the stylet 104 and cannula 102. For example, in the embodiment shown in FIGS. 5a to 5g, the coupling mechanism may provide alignment of relative rotation, flexing, translation (both axial and radial), and titling between the cannula 102 and stylet 104. In the embodiment shown in FIGS. to 9c, the coupling mechanism may provide alignment of at least the relative rotation and axial translation between the cannula 102 and the stylet 104. In the embodiment shown in FIGS. 10a and 10b, the biasing mechanism may provide alignment of the relative rotation between the cannula and stylet. The embodiment shown in FIGS. 8b 11b and 11c may provide alignment of both the flexing and rotation of the cannula and stylet. In some embodiments, alignment of only one mode of alignment may be provided. For example, an elliptical cross section portion of the body of the stylet and the lumen may provide rotational alignment only (unless combined with other embodiments of the alignment means). Based on the examples of the alignment means 126 described in this application, the skilled person would understand that suitable modifications may be made to the alignment means, or combinations of the embodiments described above may be used, to provide alignment of any one, or combination of, the different alignment modes shown in FIGS. 2a to 2e.

The process of collecting a tissue sample using the biopsy device 100 is shown in the sequence of FIGS. 12a to 12e. In this example, the biopsy device is provided with a protective outer member 146 as described above, and is used in conjunction with an endoscope. In other embodiments, the biopsy device may be used percutaneously or transluminally rather than with an endoscope.

Figure 12A:
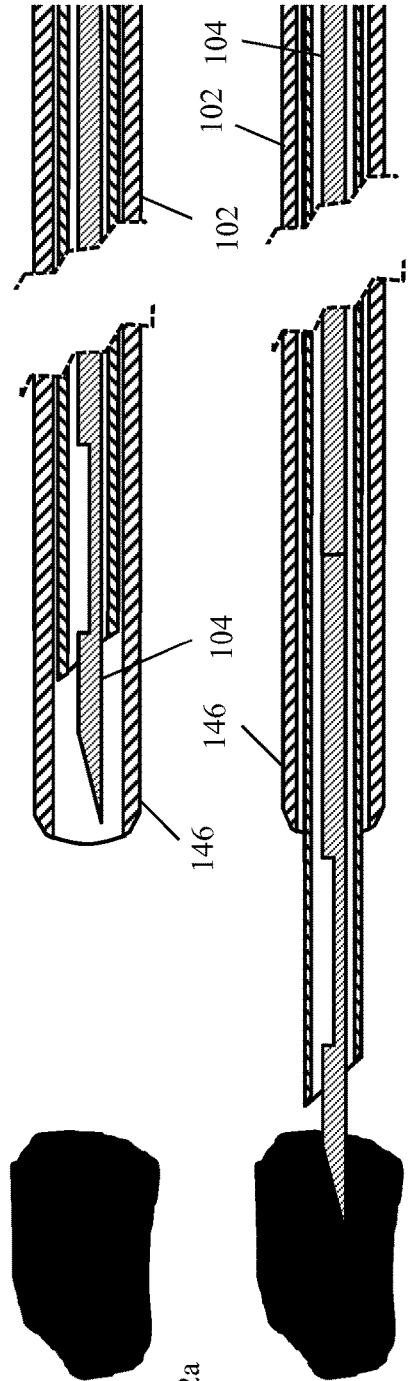

The stylet 104 and cannula 102 may begin in a retracted position in which they are both retracted within the protective outer member 146 (as shown in FIG. 12a). The outer member may reduce the risk of damaging the working channel of the endoscope when the biopsy device is passed down it.

The biopsy device 100 may be moved to the desired biopsy location by passing it through the working channel of an endoscope. During this motion of the biopsy device 100, the alignment means may act to prevent or reduce misalignment between the cannula 102 and the stylet 104. For example, the alignment means may resist or align relative rotation between the cannula 102 and the stylet 104 such that the tissue piercing portion 114 and the tissue sampling portion 122 remain aligned, despite the biopsy device 100 bending and flexing through the endoscope.

Figure 12B:
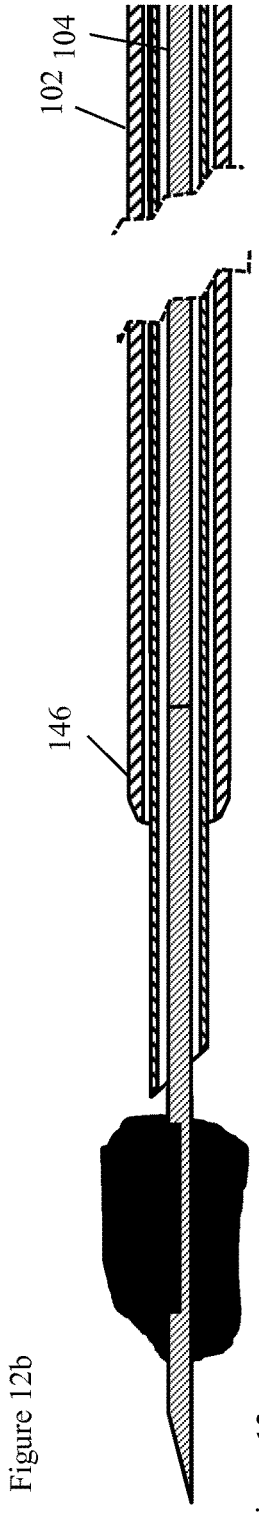

Once at the desired location, the stylet 104 and the cannula 102 may be advanced together (out of the outer member) through the surrounding tissue to reach the area from which a sample is to be taken (as shown in FIG. 12b). During this motion, the cutting portion 124 of the stylet may aid insertion through the tissue (during this movement, cannula 102 and the stylet 104 do not move relative to each other).

The biasing actuator in the control means may be primed at any time prior to stylet insertion into the tissue being sampled, including prior to insertion of the biopsy device 100 through the endoscope working channel or prior to exit of the stylet 104 and cannula 102 from the protective outer member 146 and through the tissue.

Figure 12C:
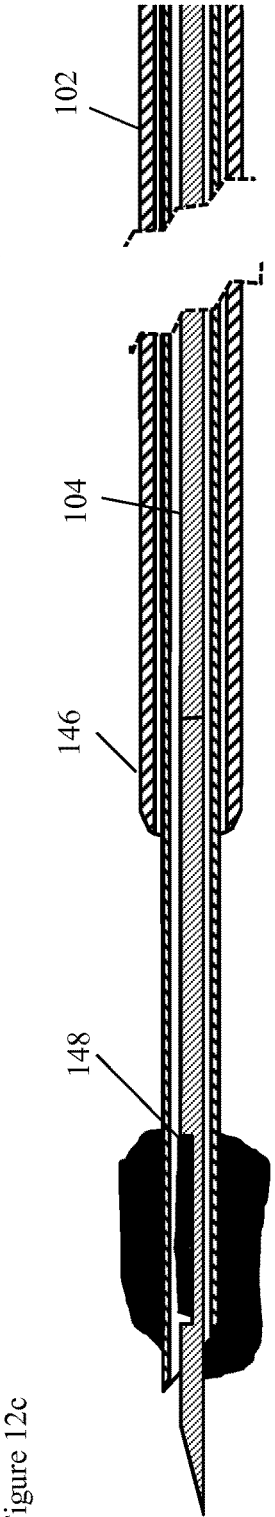
Figure 12D:
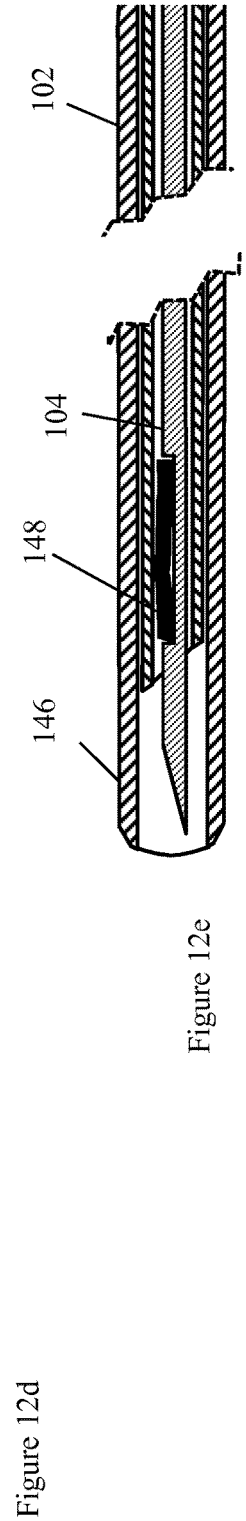
Figure 12E:
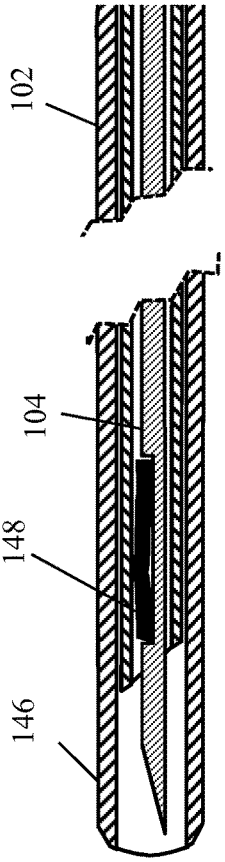

Once in position, the stylet 104 may then be moved such that it slides along the length of the lumen 112 (as shown in FIG. 12c). This advances the stylet into the area of tissue being sampled so that the tissue enters the tissue sampling portion 122. The cannula 102 may then be advanced over the stylet 104 to cut the sample of tissue 148 away from the surrounding tissue using the cutting portion 105. This leaves a sample of tissue 148 held in the tissue sampling portion 122 and covered by the cannula body 106. The cannula 102 may be advanced over the stylet 104 manually, or by the action of the biased actuator. During this motion, the alignment means may act to align the cannula and stylet so as to reduce the risk of the cutting portion 105 damaging the tissue that has been collected.

Once the tissue sample has been collected, the cannula 102 and the stylet 104 may be retracted back into the outer member 146 (e.g. so that the distal end of the stylet is flush with the end of the protective outer member 146). The biopsy device 100 may then be withdrawn out of the working channel of the endoscope and the sample 148 may be recovered for analysis.

We claim:
1. A biopsy device, comprising:
    a cannula comprising an elongate cannula body extending between a cannula distal end and a cannula proximal end to define a lumen, wherein the cannula comprises a cutting portion at the cannula distal end;
    a stylet comprising an elongate body having a stylet distal end and a stylet proximal end, the stylet being slidably disposed within the lumen, wherein the stylet comprises a tissue sampling portion;
    and at least one raised portion provided on one of the stylet or the cannula, and at least one corresponding recessed portion provided on the other of the stylet or the cannula, the at least one raised portion and the at least one recessed portion arranged to couple the cannula and the stylet, wherein:
    a sliding engagement is formed between the at least one raised portion and the at least one recessed portion whereby relative sliding between the stylet and the cannula along a longitudinal axis of the biopsy device is provided,
    the at least one raised portion and the at least one recessed portion are at least partly provided within a respective distal region of the stylet and a distal region of the cannula,
    and the sliding engagement between the at least one raised portion and the at least one recessed portion is arranged to allow the relative sliding between the stylet and the cannula while maintaining continuous mechanical engagement between the at least one raised portion and the at least one recessed portion throughout a range of sliding movement of the stylet relative to the cannula to collect a tissue sample in the tissue sampling portion, the continuous engagement being to resist movement of the cannula and the stylet away from a preferred alignment between the cutting portion of the cannula and the stylet by resisting one or both of relative rotation about the longitudinal axis or flexing between the stylet distal end and the cannula distal end.

2. The biopsy device of claim 1, wherein the at least one raised portion and the at least one recessed portion are arranged to align at least one or both of a relative position or orientation of the stylet and the cannula.

3. The biopsy device of claim 2, wherein the cannula has a preferred cutting orientation in relation to the stylet, and wherein the at least one raised portion and the at least one recessed portion are arranged to align the cannula and stylet in the preferred cutting orientation relative to each other.

4. The biopsy device of claim 1, wherein the stylet has a preferred plane of flexibility, and wherein the at least one raised portion and the at least one recessed portion are arranged to resist relative movement between the stylet and the cannula in the preferred plane of flexibility.

5. The biopsy device according to claim 1, wherein one or more of:
    the at least one recessed portion comprises a groove extending part way through the elongate body of the cannula or the elongate body of the stylet;
    the at least one recessed portion comprises a slot extending through the elongate body of the cannula or the elongate body of the stylet;
    the at least one raised portion comprises at least one pin arranged to be received in the recessed portion;
    the at least one raised portion comprises at least one ridge on the elongate body of the cannula or the stylet arranged to be received in the recessed portion.

6. The biopsy device according to claim 1:
    wherein the at least one recessed portion defines a first abutment surface and the at least one raised portion defines a second abutment surface, wherein contact between the first and second abutment surfaces resists relative flexing movement between the stylet and the cannula, and preferably resists relative flexing in a preferred plane of flexibility of the stylet.

7. The biopsy device according to claim 1:
    wherein the at least one recessed portion defines a first distal stop surface and/or a first proximal stop surface, and the at least one raised portion defines a second distal stop surface and/or a second proximal stop surface, wherein contact between the first and second proximal or distal stop surfaces restricts axial movement between the stylet and the cannula along the longitudinal axis of the biopsy device.

8. The biopsy device according to claim 1, wherein the distal region of the cannula extends a distance from the cannula distal end and the distal region of the stylet extends a distance from the stylet distal end, and any one or more of:
    the distance which the distal region of the cannula extends from the cannula distal end is 25% of the distance between the cannula distal end and the cannula proximal end;
    the distance which the distal region of the stylet extends from the stylet distal end is 25% of the distance between the stylet distal end and the stylet proximal end;
    the distance which the distal region of the cannula extends from the cannula distal end is up to or equal to 50 mm;
    the distance which the distal region of the stylet extends from the stylet distal end is up to or equal to 50 mm; and/or
    wherein the stylet distal region comprises a region of the stylet extending between the stylet distal end and a distal end of the tissue sampling portion.

9. The biopsy device according to claim 1, wherein:
    the tissue sampling portion comprises a recess in the elongate body of the stylet in which tissue is received;
    the at least one recessed portion is provided on the stylet and the at least one raised portion is provided on the cannula, the at least one recessed portion of the stylet defining an abutment surface arranged to slidably engage with the at least one raised portion of the cannula; and
    a surface of the recess forming the tissue sampling portion forms part of the abutment surface of the stylet within the extent of the tissue sampling portion.

10. The biopsy device according to claim 1, wherein the at least one raised portion or the at least one recessed portion or both extend along the stylet or the cannula to form the sliding engagement between the at least one raised portion and the at least one recessed portion.

11. The biopsy device of claim 1, wherein the cannula proximal end and the stylet proximal end are rotationally uncoupled.

12. The biopsy device according to claim 1, further comprising an actuator arranged to control the relative sliding between the cannula and the stylet to allow a tissue sample to be taken, and wherein the actuator is arranged to link the cannula proximal end and the stylet proximal end to control relative axial sliding between them and to allow relative rotation between the cannula proximal end and the stylet proximal end.

13. The biopsy device of claim 1, wherein a portion of the elongate body of the stylet and a portion of the lumen of the cannula each having a corresponding non-circular cross section, wherein engagement between the cannula body and the stylet body resists relative rotation between them.

14. The biopsy device of claim 1, wherein the cutting portion comprises a tissue piercing portion, and the at least one raised portion and the at least one recessed portion are arranged to prevent or minimise flexing of the cannula in a first direction towards the stylet to prevent or minimise movement of the tissue piercing portion towards the tissue sampling portion.

15. The biopsy device of claim 1, wherein the at least one raised portion and the at least one recessed portion are further arranged to align one or more of:
   i) relative tilting between the stylet and the cannula;
   ii) relative radial translation between the stylet and the cannula;
   iii) relative axial translation between the stylet distal end and the cannula distal end.

\* \* \* \* \*